US012613250B2

(12) United States Patent
Elie et al.

(10) Patent No.: US 12,613,250 B2
(45) Date of Patent: Apr. 28, 2026

(54) BIOMARKER PANEL FOR SEPSIS ENCEPHALOPATHY

(71) Applicant: UNIVERSITY OF FLORIDA RESEARCH FOUNDATION, INC., Gainesville, FL (US)

(72) Inventors: Marie C. Elie, Gainesville, FL (US); Scott A. Cohen, Gainesville, FL (US); Zhihui Yang, Gainesville, FL (US); Kevin Ka W Wang, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 1155 days.

(21) Appl. No.: 17/608,027

(22) PCT Filed: Apr. 30, 2020

(86) PCT No.: PCT/US2020/030671
§ 371 (c)(1),
(2) Date: Nov. 1, 2021

(87) PCT Pub. No.: WO2020/223462
PCT Pub. Date: May 11, 2020

(65) Prior Publication Data
US 2022/0317135 A1      Oct. 6, 2022

Related U.S. Application Data

(60) Provisional application No. 62/841,000, filed on Apr. 30, 2019.

(51) Int. Cl.
G01N 33/68      (2006.01)

(52) U.S. Cl.
CPC ................................ G01N 33/6896 (2013.01)

(58) Field of Classification Search
None
See application file for complete search history.

(56) References Cited

U.S. PATENT DOCUMENTS

2014/0342381 A1  11/2014  Hayes
2015/0141528 A1*  5/2015  Larner ................ G01N 33/6896
                                                    514/789
2016/0166598 A1   6/2016  Dobson
2016/0178643 A1   6/2016  Everett et al.
2017/0014450 A1   1/2017  Joyce et al.

FOREIGN PATENT DOCUMENTS

WO      2020223462 A1    11/2020

OTHER PUBLICATIONS

Hsu et al (Pediatric Critical Care Medicine 9:245-51) (Year: 2008).*
PCT Search Report & Written Opinion PCT/US2020/030671, date mailed Oct. 1, 2020, 11 pages.
Annane, Dijillali et al., "Cognitive decline after sepsis", www.thelancet.com/respiratory, vol. 3, Jan. 2015, pp. 61-69.
Douglas-Escobar, Martha et al., "Biomarkers of hypoxic-ischemic encephalopathy in newborns", Frontiers in Neurology, vol. 3, article 144, Nov. 2, 2012, 5 pages.
Ehler, Johannes et al., "The prognostic value of neurofilament levels in patients with sepsis-associated encephalopathy—A prospective, pilot observational study", PLos One, Jan. 24, 2019, 17 pages.
Eidelman, Leonid A. et al., "The Spectrum of Septic Encephalopathy", JAMA, Feb. 14, 1996, vol. 275, No. 6, pp. 470-473.
Hughes, Christopher G. et al., "Relationships between Markers of Neurologic and Endothelial Injury during Critical Illness and Long-Term Cognitive Impairment and Disability", Intensive Care Med., Mar. 2018, vol. 44, No. 3, pp. 345-355.
Lagu, Tara et al., "Hospitalizations, costs, and outcomes of severe sepsis in the United States 2003 to 2007", Crit. Care Med., 2012, vol. 40, No. 3, pp. 754-761.
Marcantonio, Edward R. et al., "Serum Biomarkers for Delirium", Journal of Gerontology: Medical Sciences, 2006, vol. 61A, No. 12, pp. 1281-1286.
Pratt, Alexandera K. et al., "A Fate Worse Than Death: Prognostication of Devastating Brain Injury", Critical Care Medicine, vol. 47, No. 4, Apr. 2019, 591-598.
Widmann, Catherine N. et al., "Long-term cerebral consequences of sepsis", Lancet Neurol, 2014, vol. 13, pp. 630-636.
Zhang, Qing-Hong et al., "Septic encephalopathy: when cytokines interact with acethylcholine in the brain", Military Research, 2014, vol. 1, No. 20, 9 pages.

* cited by examiner

*Primary Examiner* — Christopher M Gross
(74) *Attorney, Agent, or Firm* — Timothy H. Van Dyke; Wolter Van Dyke Davis, PLLC

(57) ABSTRACT

This invention provides methods of detecting biomarkers in the biofluid of sepsis-associated encephalopathy (SAE) patients, including but not limited to glial fibrillary acidic protein (GFAP), ubiquitin C-terminal hydrolase LI, Tan protein, Neurofilament light chain (NF-L), myelin basic protein (MBP), secretogranin, Copeptin, total all-spectrin, all-spectrin breakdown products (SBDP, including SBDP145, SBDP150, SBDP120 all-spectrin N-terminal fragment or SBDP150N), neuron specific enolase (NSE), mature brain derived neurotrophic factor (BDNF), and full-length Pro-BDNF. These biomarker peptides are markers of axonal and blood brain barrier integrity which can be used to diagnose SAE and to assess and predict cognitive performance and outcomes in acute presentations of sepsis.

3 Claims, 31 Drawing Sheets

FIG. 1

S100b - Hours After Enrollment: 72

$\log_e(W) = 1.39, p = 0.055, r = 0.61, CI_{95\%} [0.27, 1.00], n = 11$ pNFH - Hours After Enrollment: Baseline $\log_e(W) = 4.61, p = 0.039, r = 0.44, CI_{95\%} [0.06, 0.83], n = 23$ UCHL1 - Hours After Enrollment: 6

$\log_e(W) = 4.66$, $p = 0.015$, $r = 0.51$, $CI_{95\%}$ [0.19, 0.82], $n = 23$

UCLH-1 Concentration [pg/mL]

600

400

200

0

217.65

55.08

1
(n = 11)

2
(n = 12)

Cohort Assignment

UCHL1 - Hours After Enrollment: Baseline $\log_e(W) = 4.63$, $p = 0.005$, $r = 0.60$, $CI_{95\%}$ [0.37, 0.88], $n = 22$ UCLH-1 Concentration [pg/mL]

600

400

200

0

282.47

52.19

1
(n = 10)

2
(n = 12)

Cohort Assignment

*Outlier Not Included From Cohort 1: Concentration > 4000 pg/mL

UCHL1 - Hours After Enrollment: 18

$\log_e(W) = 4.52$, $p = 0.010$, $r = 0.57$, $CI_{95\%}$ [0.29, 0.88], $n = 21$

UCHL1 - Hours After Enrollment: 12

$\log_e(W) = 4.62$, $p = 0.008$, $r = 0.58$, $CI_{95\%}$ [0.31, 0.90], $n = 22$ pNFH - Ratio Between Hours: 24 and Baseline $\log_e(W) = 2.83$, $p = 0.029$, $r = 0.51$, $CI_{95\%}$ [0.21, 0.81], $n = 19$ UCHL1 - Hours After Enrollment: 72

$\log_e(W) = 3.00$, $p = 0.144$, $r = 0.50$, $CI_{95\%}$ [0.06, 0.94], $n = 10$

S100b - Ratio Between Hours: 72 and Baseline $\log_e(W) = 1.79, p = 0.121, r = 0.50, CI_{95\%} [0.05, 0.88], n = 11$ pNFH - Ratio Between Hours: 72 and Baseline $\log_e(W) = 1.39, p = 0.031, r = 0.65, CI_{95\%} [0.28, 1.10], n = 12$

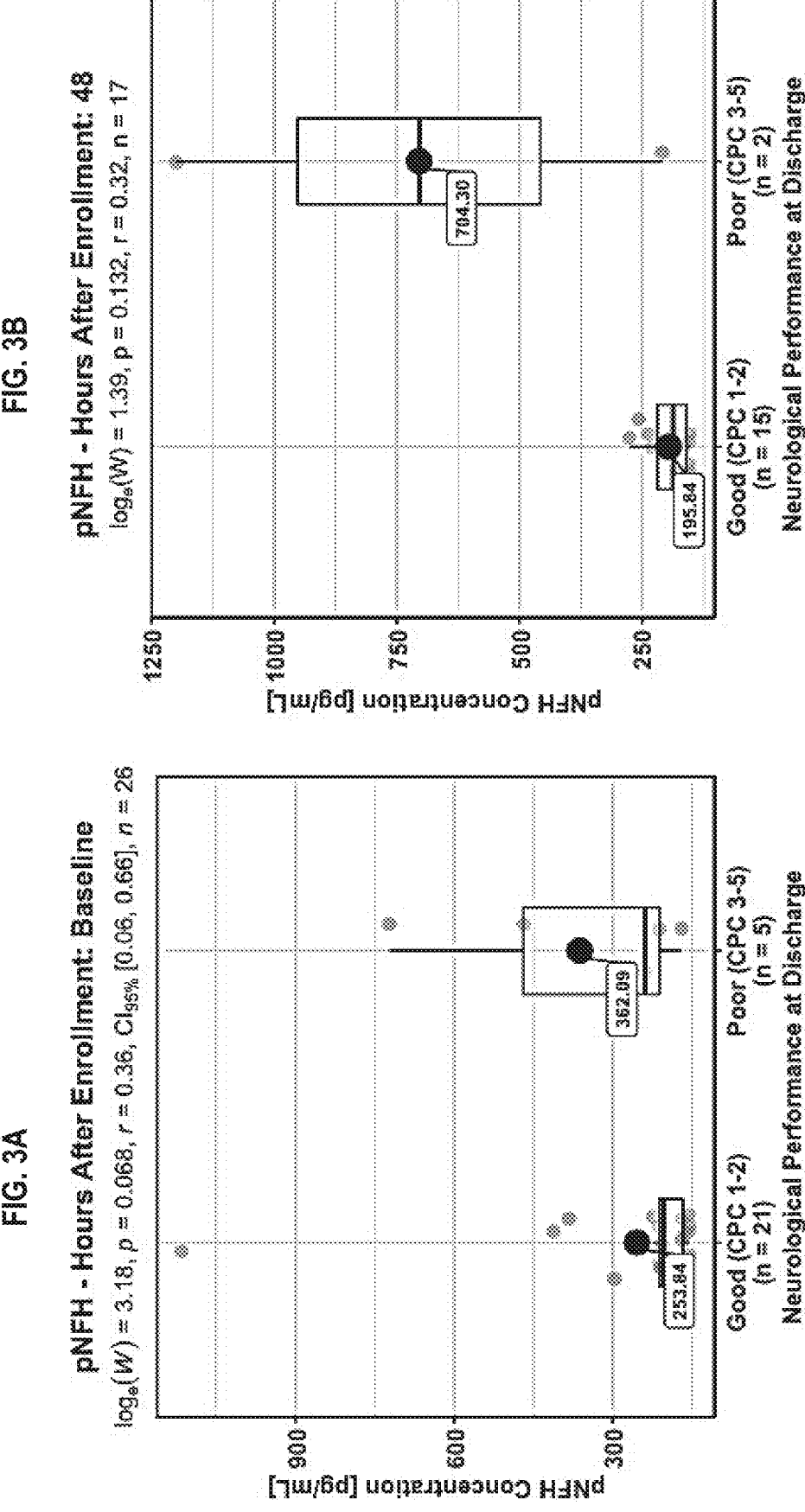

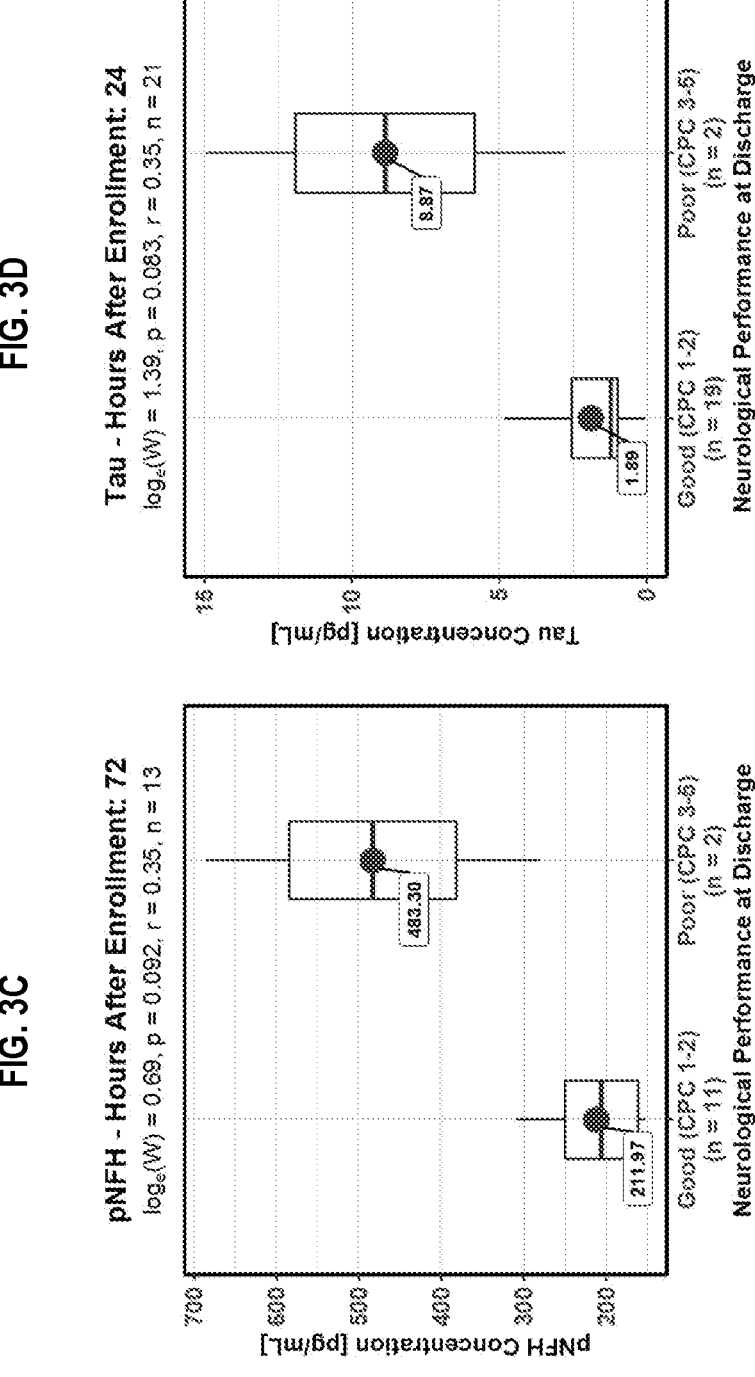

Figures 3G, 3H:
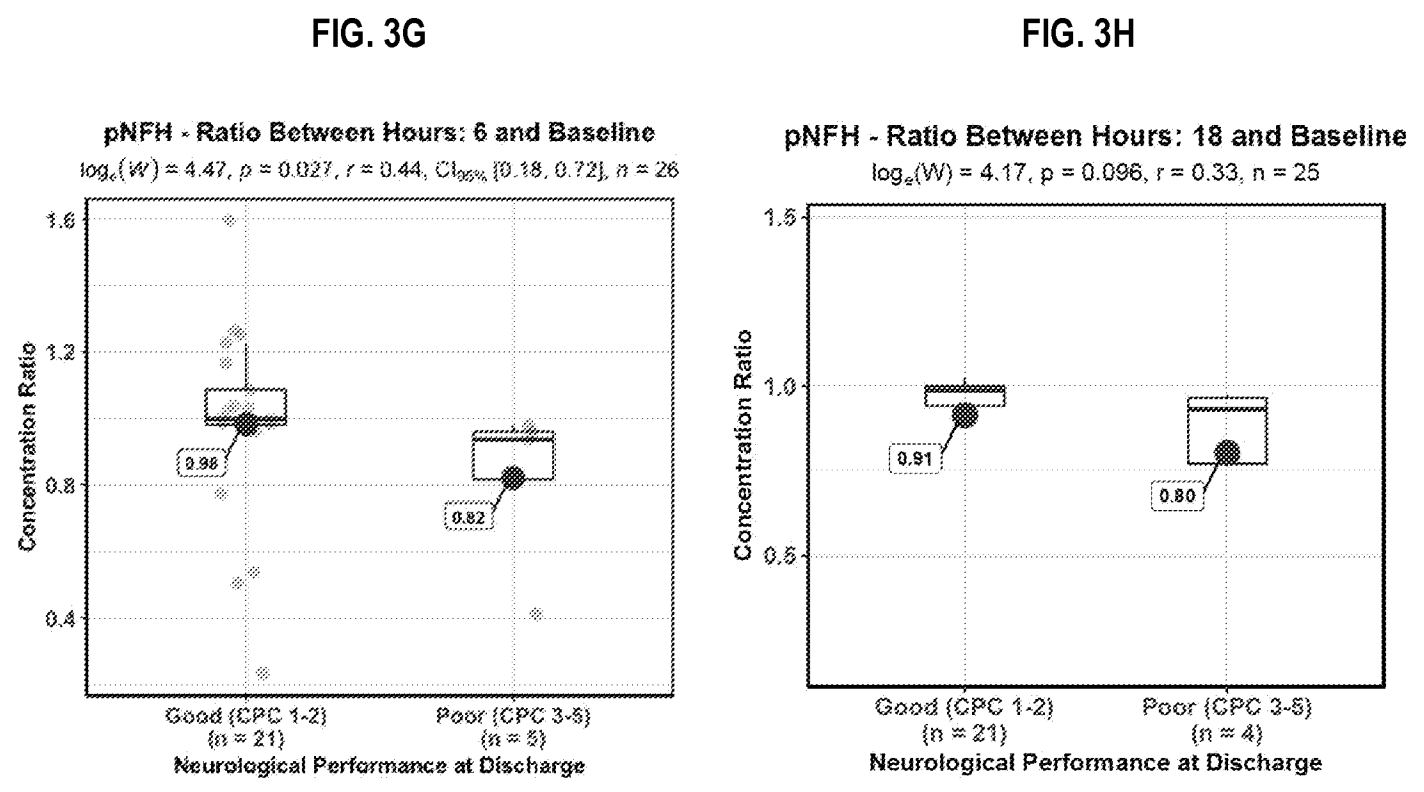

FIG. 3H pNFH - Ratio Between Hours: 18 and Baseline
$\log_e(W) = 4.17$, $p = 0.096$, $r = 0.33$, $n = 25$

FIG. 3G pNFH - Ratio Between Hours: 6 and Baseline
$\log_e(W) = 4.47$, $p = 0.027$, $r = 0.44$, $CI_{95\%}$ [0.18, 0.72], $n = 26$

FIG. 3J

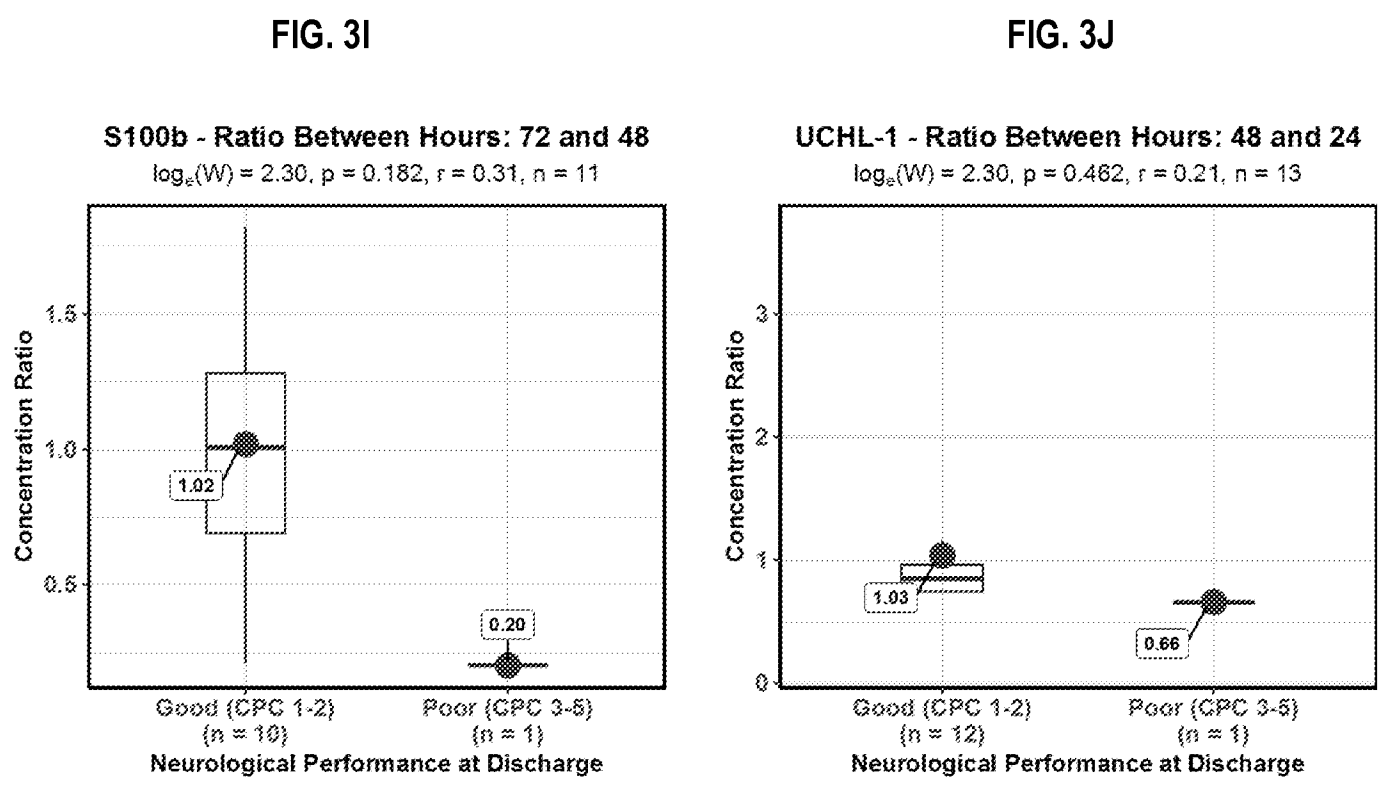

UCHL-1 - Ratio Between Hours: 48 and 24

$\log_e(W) = 2.30$, $p = 0.462$, $r = 0.21$, $n = 13$

Concentration Ratio 0.66

1.03

Good (CPC 1-2)
(n = 12)

Poor (CPC 3-5)
(n = 1)

Neurological Performance at Discharge

FIG. 3I

S100b - Ratio Between Hours: 72 and 48

$\log_e(W) = 2.30$, $p = 0.182$, $r = 0.31$, $n = 11$

Concentration Ratio 1.02

0.20

Good (CPC 1-2)
(n = 10)

Poor (CPC 3-5)
(n = 1)

Neurological Performance at Discharge

FIG. 3L

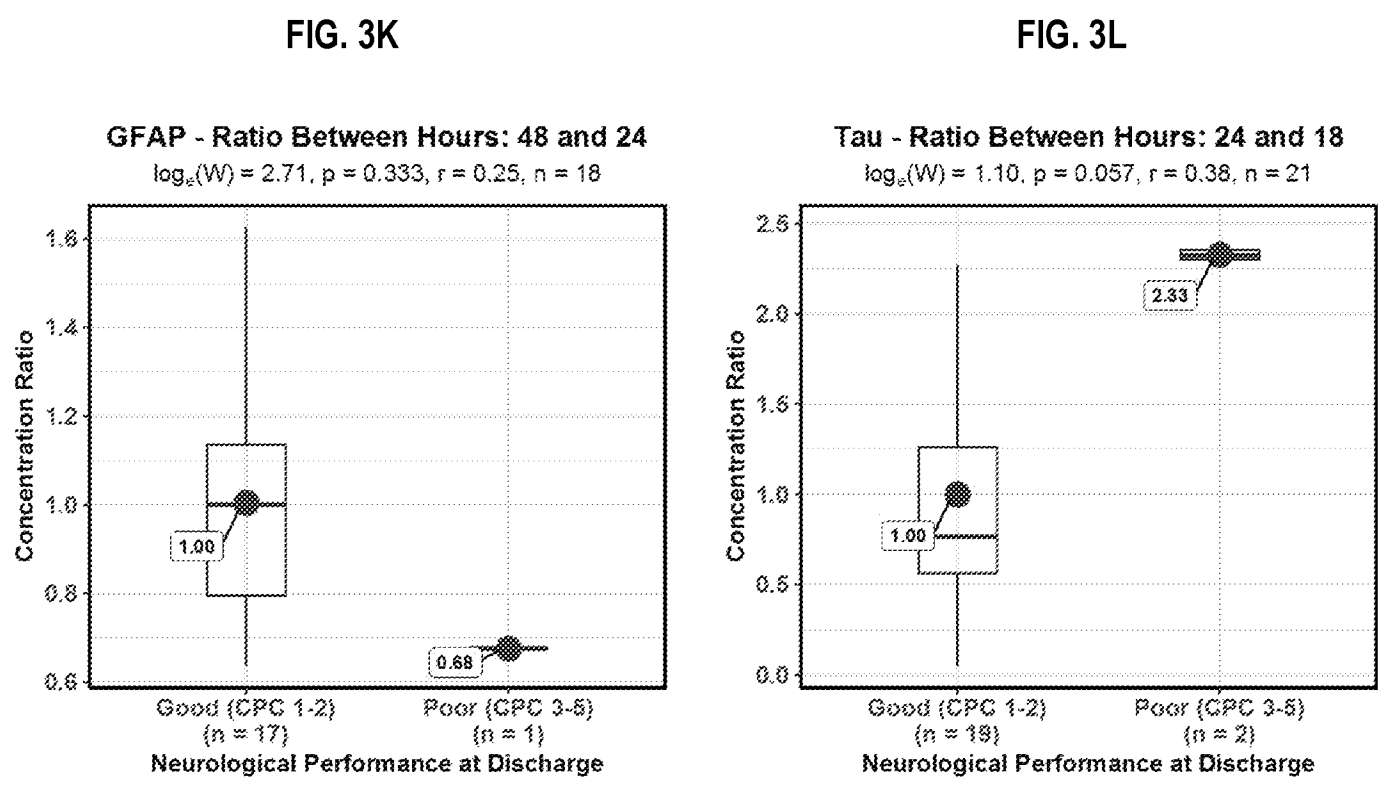

Tau - Ratio Between Hours: 24 and 18
$\log_e(W) = 1.10, p = 0.057, r = 0.38, n = 21$ 2.33

1.00

Concentration Ratio

Good (CPC 1-2)          Poor (CPC 3-5)
(n = 19)                (n = 2)
Neurological Performance at Discharge

FIG. 3K

GFAP - Ratio Between Hours: 48 and 24
$\log_e(W) = 2.71, p = 0.333, r = 0.25, n = 18$ 1.00

0.68

Concentration Ratio

Good (CPC 1-2)          Poor (CPC 3-5)
(n = 17)                (n = 1)
Neurological Performance at Discharge

FIG. 3N

NF-L - Ratio Between Hours: 72 and 48

$\log_e(W) = 2.64$, $p = 0.179$, $r = 0.31$, $n = 10$

FIG. 3M

Tau - Ratio Between Hours: 48 and 24

$\log_e(W) = 2.71$, $p = 0.333$, $r = 0.25$, $n = 18$

FIG. 3P

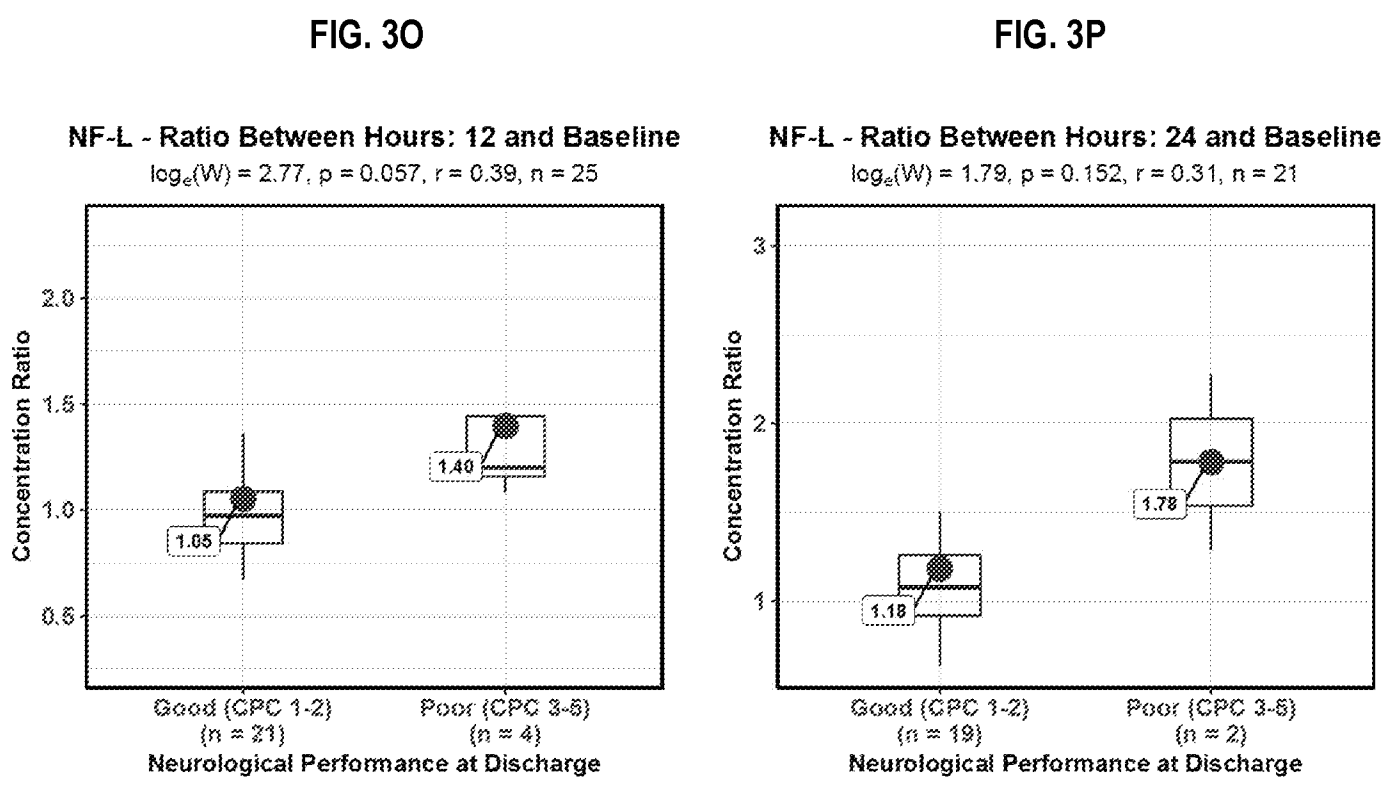

NF-L – Ratio Between Hours: 24 and Baseline

$\log_e(W) = 1.79, p = 0.152, r = 0.31, n = 21$

Concentration Ratio 1.78

1.18

Good (CPC 1-2)
(n = 19)

Poor (CPC 3-5)
(n = 2)

Neurological Performance at Discharge

FIG. 3O

NF-L – Ratio Between Hours: 12 and Baseline

$\log_e(W) = 2.77, p = 0.057, r = 0.39, n = 25$

Concentration Ratio 1.40

1.05

Good (CPC 1-2)
(n = 21)

Poor (CPC 3-5)
(n = 4)

Neurological Performance at Discharge

FIG. 4B

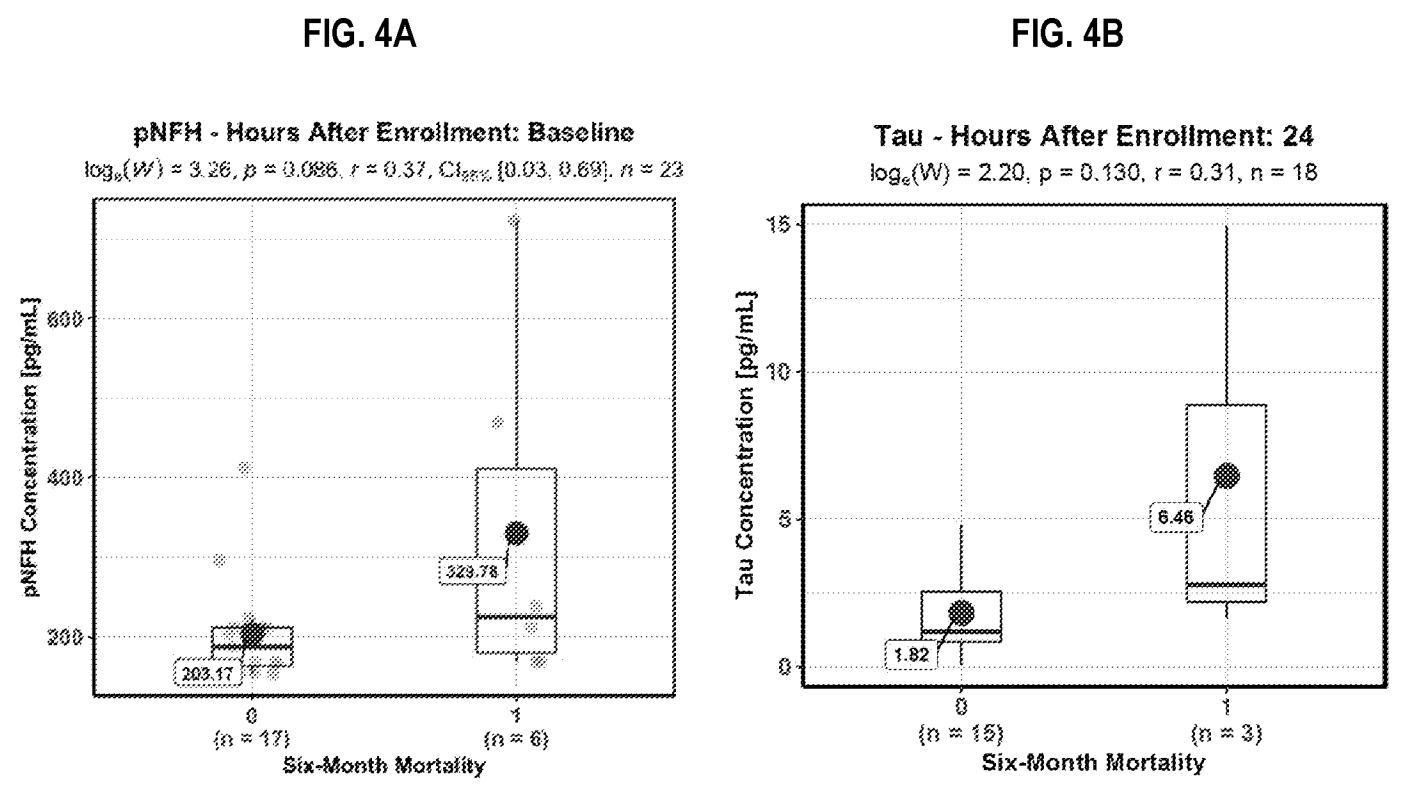

Tau - Hours After Enrollment: 24

$\log_e(W) = 2.20$, $p = 0.130$, $r = 0.31$, $n = 18$ 6.46

1.82

(n = 3)

(n = 15)

Six-Month Mortality

Tau Concentration [pg/mL]

15

10

5

0

FIG. 4A pNFH - Hours After Enrollment: Baseline $\log_{10}(W) = 3.26$, $p = 0.086$, $r = 0.37$, $CI_{95\%}$ [0.03, 0.69], $n = 23$ 323.78

203.17

(n = 6)

(n = 17)

Six-Month Mortality pNFH Concentration [pg/mL]

NF-L - Hours After Enrollment: 6

$\log_e(W) = 3.26, p = 0.113, r = 0.35, CI_{95\%}$ [0.06, 0.67], $n = 2$

FIG. 4C

Tau - Hours After Enrollment: 72

$\log_e(W) = 1.39, p = 0.133, r = 0.32, n = 11$

FIG. 4H

S100b - Ratio Between Hours: 72 and 48

FIG. 4G

S100b - Ratio Between Hours: 48 and 24

FIG. 4N

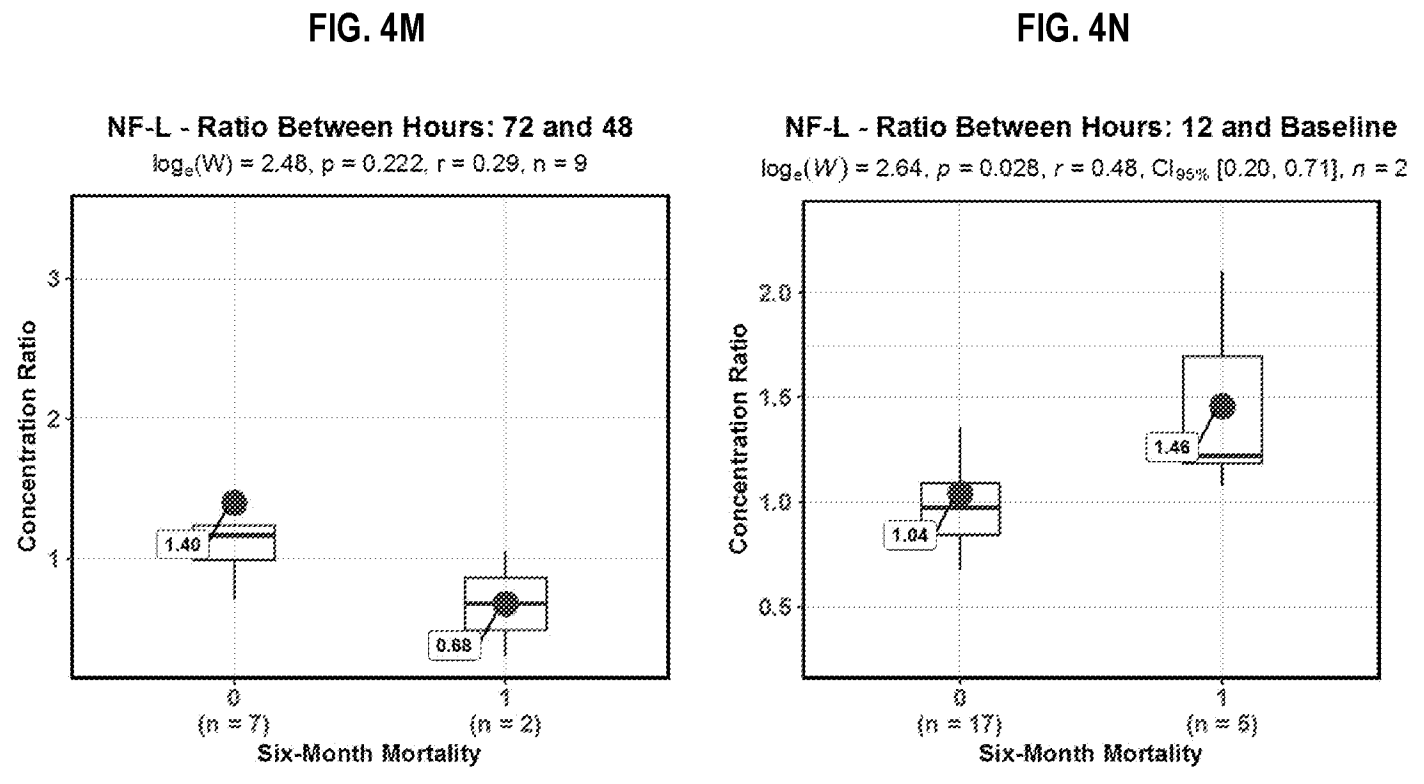

NF-L – Ratio Between Hours: 12 and Baseline $\log_e(W) = 2.64$, $p = 0.028$, $r = 0.48$, $CI_{95\%}$ [0.20, 0.71], $n = 2$

FIG. 4M

NF-L – Ratio Between Hours: 72 and 48

$\log_e(W) = 2.48$, $p = 0.222$, $r = 0.29$, $n = 9$

FIG. 4P

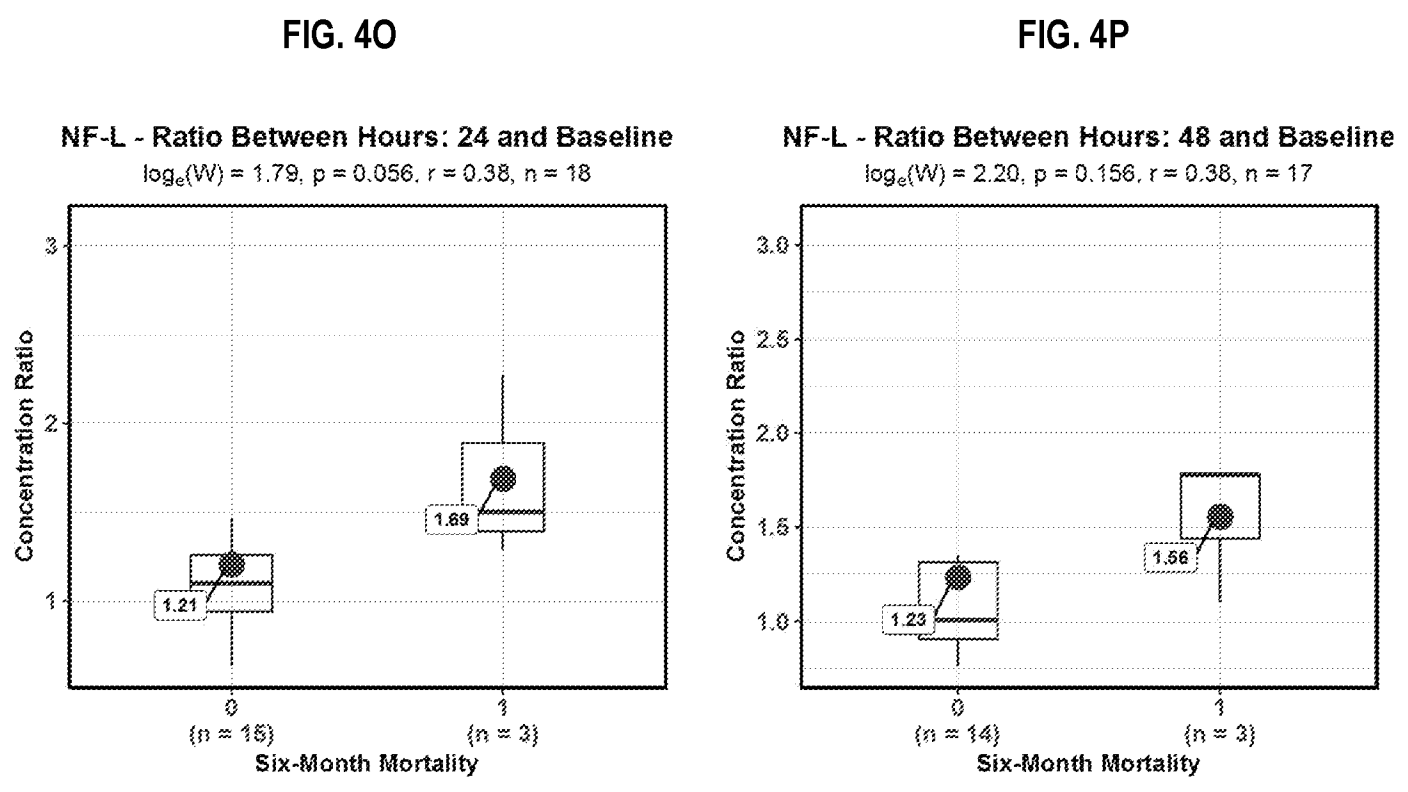

NF-L - Ratio Between Hours: 48 and Baseline $\log_e(W) = 2.20$, p = 0.156, r = 0.38, n = 17

FIG. 4O

NF-L - Ratio Between Hours: 24 and Baseline $\log_e(W) = 1.79$, p = 0.056, r = 0.38, n = 18

BIOMARKER PANEL FOR SEPSIS ENCEPHALOPATHY

CROSS-REFERENCE TO RELATED APPLICATIONS

This application claims the benefit of U.S. provisional application Ser. No. 62/841,000, filed 30 Apr. 2019. The entire contents of this application is hereby incorporated by reference as if fully set forth herein.

BACKGROUND

1. Field

The invention relates to the field of medicine, and in particular to methods for diagnosis, prognosis, and management of sepsis and other critical issues, such as a medical or surgical event rendering a risk to limb, organ, or life. In particular, the invention relates to a panel of sepsis-associated encephalopathy biomarkers that are released from injured tissues into biofluids such as blood, and their use as markers for detection of sepsis-associated encephalopathy (SAE).

2. Background

Sepsis, a syndrome characterized by a severe infection and a maladaptive inflammatory response remains the principal cause of death in US hospitals, with approximately 250,000 deaths annually and costing over $18 billion per year. Martin et al., N. Engl. J. Med. 348:1546-54, 2003; Lagu et al., Crit. Care Med. 40:754-61, 2012. Delirium or altered mental status (AMS) represents a prevalent symptom associated with sepsis, in up to 70% of acute presentations, understood to be an independent predictor of death. Gofton et al., Nat. Rev. Neurol. 8:557-66, 2012; Eidelman et al., JAMA 275:470-3. 1996. In fact, an acute cognitive disturbance in the setting of sepsis or Sepsis Associated Encephalopathy (SAE) is often the sole presenting symptom in many patients. Numerous purported mechanisms have been suggested as mechanistic pathways for SAE including inflammation, a disrupted blood-brain barrier, oxidative stress, and severe microglial activation, however the cause remains unclearly defined. Annane and Sharshar, Lancet Respir. Med. 3:61-9, 2015. Traditionally, the onset of SAE was thought to be largely reversible with the resolution of the underlying infection, however numerous studies over the past decade cite long term cognitive deficits. Annane and Sharshar, Lancet Respir. Med. 3:61-9, 2015; Iwashyna et al., JAMA 304:1787-94, 2010. These deficits range from subjective complaints of "fogginess" to dementia-like syndromes analogous to Alzheimer's. Iwashyna et al., JAMA 304:1787-94, 2010; Widmann and Heneka, Lancet Neurol. 13:630-6, 2014.

SAE can be a confounding syndrome for physicians to diagnose, especially in the absence of any other symptoms of inflammation. Among the elderly, altered mentation is frequently the only and primary symptom presenting with a diagnosis of sepsis, delaying the evaluation for an infection by hours or days. To date, there are no diagnostic tests available to clinicians to reliably diagnose SAE in patients. Moreover, SAE is distressing to both the patient and caregiver, and yet clinical providers lack appropriate tools to define the etiology, treat or predict recovery. The challenges encountered by clinicians to communicate long term prognosis regarding long term cognitive decline is described by Pratt et al where they characterize long term brain injury as a "fate worse than death" by patients and caregivers. Pratt et al., Crit. Care Med. 47:591-8, 2019. However, there are no existing tools available to support physicians and other clinicians in providing a diagnosis nor prognosis in the hospital setting, where invasive and expensive procedures performed may not have the benefit of improving outcomes. This renders a high degree of uncertainty in shared clinician patient decision making. Evans et al., Am. J. Respir. Crit. Care Med. 179:48-53, 2009. To date, there have been no contemporary serum biomarker available for the diagnosis, management or prognosis of an altered mental state related to sepsis associated encephalopathy.

SUMMARY

Now, it has been discovered that certain biomarkers can be detected in biofluid of SAE patients, including but not limited to Glial fibrillary acidic protein (GFAP), ubiquitin C-terminal hydrolase L1 (UCHL-1), 5100 calcium-binding protein B (S100B), Tau protein, Neurofilament light chain (NF-L) and phosphorylated neurofilament heavy chain (pNFH). These biomarker peptides are markers of axonal and blood brain barrier integrity which can be used to diagnose the condition and to assess and predict cognitive performance and outcomes in acute presentations of sepsis.

Specifically, certain embodiments of the invention relates to a method for detecting one or more biomarkers in a biological sample comprising: detecting whether a phosphoneurofilament-H (pNF-H), S100 calcium-binding protein B (S100B), or both are present in a biological sample collected from a subject suffering from sepsis-associated encephalopathy (SAE) or suspected of suffering from SAE by (a) contacting the biological sample with at least one antibody recognizing pNFH, S100B, or both; and (b) detecting binding of the antibody to glial fibrillary acidic protein (GFAP), ubiquitin C-terminal hydrolase L1, Tau protein, Neurofilament light chain (NF-L), myelin basic protein (MBP), secretogranin, Copeptin, total $\alpha$II-spectrin, $\alpha$II-spectrin breakdown products (SBDP, including SBDP145, SBDP150, SBDP120 $\alpha$II-spectrin N-terminal fragment or SBDP150N), neuron specific enolase (NSE), mature brain derived neurotrophic factor (BDNF), and full-length Pro-BDNF.

In other embodiments, the invention relates to a method of improving diagnosis of SAE in a subject in need thereof, comprising:

(a) collecting a biological sample from the subject within about 6 hours from arrival at a treatment facility, within about 72 hours from arrival at a treatment facility, or both; and (b) testing the sample or samples for the presence or amount of a first biomarker and a second biomarker, wherein the first biomarker is selected from the group consisting of GFAP, UCH-L1, NF-L, and pNF-H; and the second biomarker is selected from the group consisting of GFAP, NF-L, pNF-H, UCH-L1, Tau, secretogranin, MBP, $\alpha$II-spectrin, SBDP, NSE, BDNF, and Pro-BDNF.

In some embodiments, the first biomarker is GFAP and the second biomarker is UCH-L1, or the first biomarker is NF-L and the second biomarker is pNF-H.

In other embodiments, the invention relates to a method of providing a prognosis of neurological outcome or mortality of SAE in a subject in need thereof, comprising:

(a) collecting a biological sample from the subject within about 6 hours from arrival at a treatment facility, within about 72 hours from arrival at a treatment facility, or both; and (b) testing the sample or samples for the presence or amount of a first biomarker and a second biomarker, wherein the first biomarker is selected from the group consisting of GFAP, Tau, or S100B, and pNF-H; and the second biomarker is selected from the group consisting of GFAP, NF-L, pNF-H, UCH-L1, Tau, secretogranin, MBP, αII-spectrin, SBDP, NSE, BDNF, and Pro-BDNF. Advantageously, the first biomarker is GFAP and the second biomarker is Tau, or the first biomarker is GFAP and the second biomarker is S100B, or the first biomarker is GFAP and the second biomarker is NF-L1.

In other embodiments, the invention relates to a method of improving diagnosis of SAE in a subject in need thereof, comprising:

(a) collecting a biological sample from the subject at two time points selected from the group consisting of within about 6 hours from arrival at a treatment facility, within about 12 hours from arrival at a treatment facility, at about 24 hours from arrival at a treatment facility, at about 48 hours from arrival at a treatment facility, and at about 72 hours from arrival at a treatment facility;

(b) testing the samples for the presence or amount of at least one biomarker; and (c) determining the change in the biomarker amount between the two sample times, wherein the at least one biomarker is selected from the group consisting of UCH-L1, pNF-H, S100B, GFAP, NFL, and Tau. Advantageously, the collecting is performed at within about 6 hours from arrival at a treatment facility and at about 72 hours after arrival at a treatment facility or the collecting is performed at within about 6 hours from arrival at a treatment facility and at about 48 hours after arrival at a treatment facility.

In further embodiments, the invention pertains to a method of providing a prognosis of neurological outcome or mortality of SAE in a subject in need thereof, comprising:

(a) collecting a biological sample from the subject at two time points selected from the group consisting of within about 6 hours from arrival at a treatment facility, within about 12 hours from arrival at a treatment facility, at about 24 hours from arrival at a treatment facility, at about 48 hours from arrival at a treatment facility, and at about 72 hours from arrival at a treatment facility;

(b) testing the samples for the presence or amount of at least one biomarker; and (c) determining the change in the biomarker amount between the two sample times, wherein the at least one biomarker is selected from the group consisting of UCH-L1, pNF-H, S100B, GFAP, NFL, and Tau. Advantageously, the collecting is performed at within about 6 hours from arrival at a treatment facility and at about 72 hours after arrival at a treatment facility or the collecting is performed at within about 6 hours from arrival at a treatment facility and at about 48 hours after arrival at a treatment facility or the collecting is performed at within about 6 hours from arrival at a treatment facility and at about 24 hours after arrival at a treatment facility, or the collecting is performed at about 24 hours from arrival at a treatment facility and at about 48 hours after arrival at a treatment facility.

BRIEF SUMMARY OF THE DRAWINGS

FIG. 1 is a flow chart of study procedures.

5

Figures 4C, 4D:
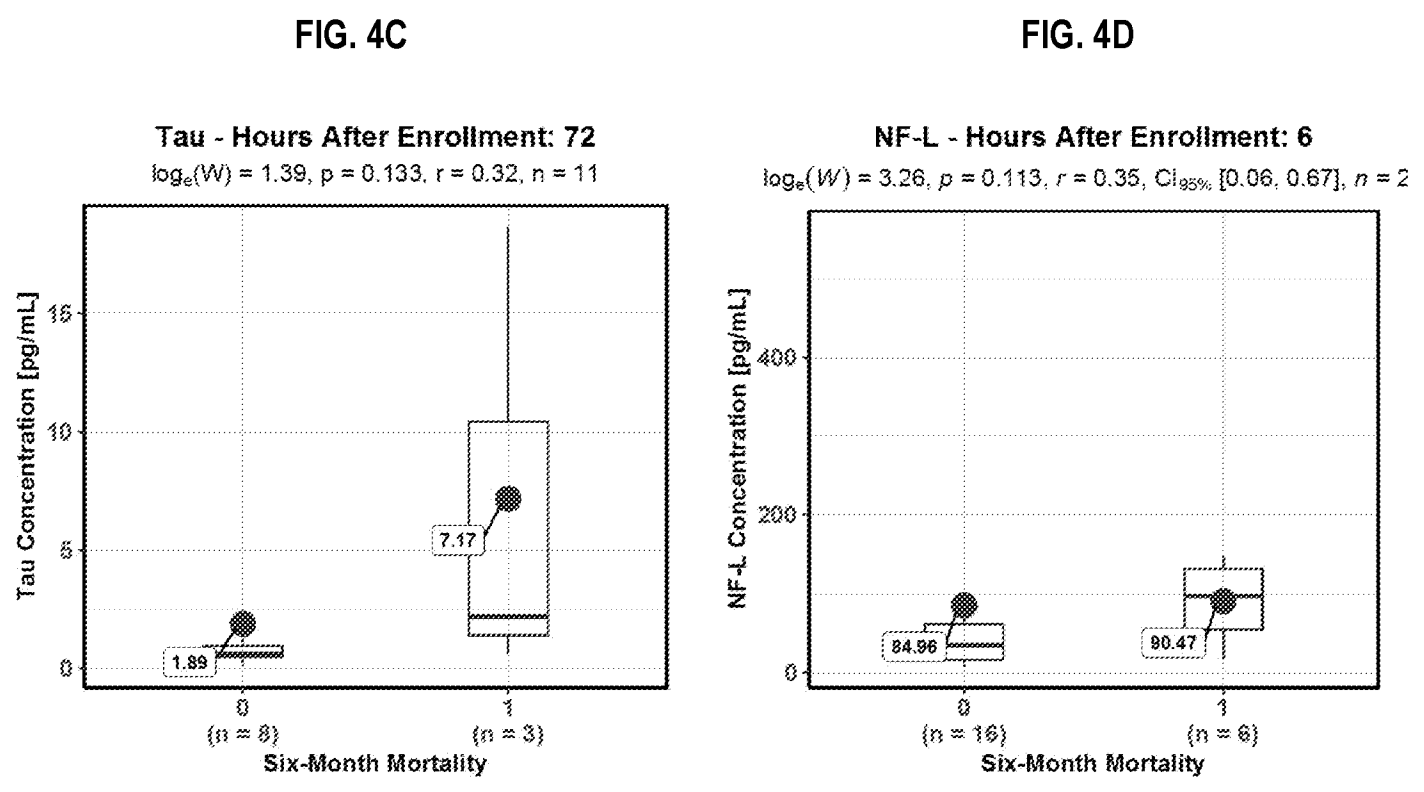
Figures 4E, 4F:
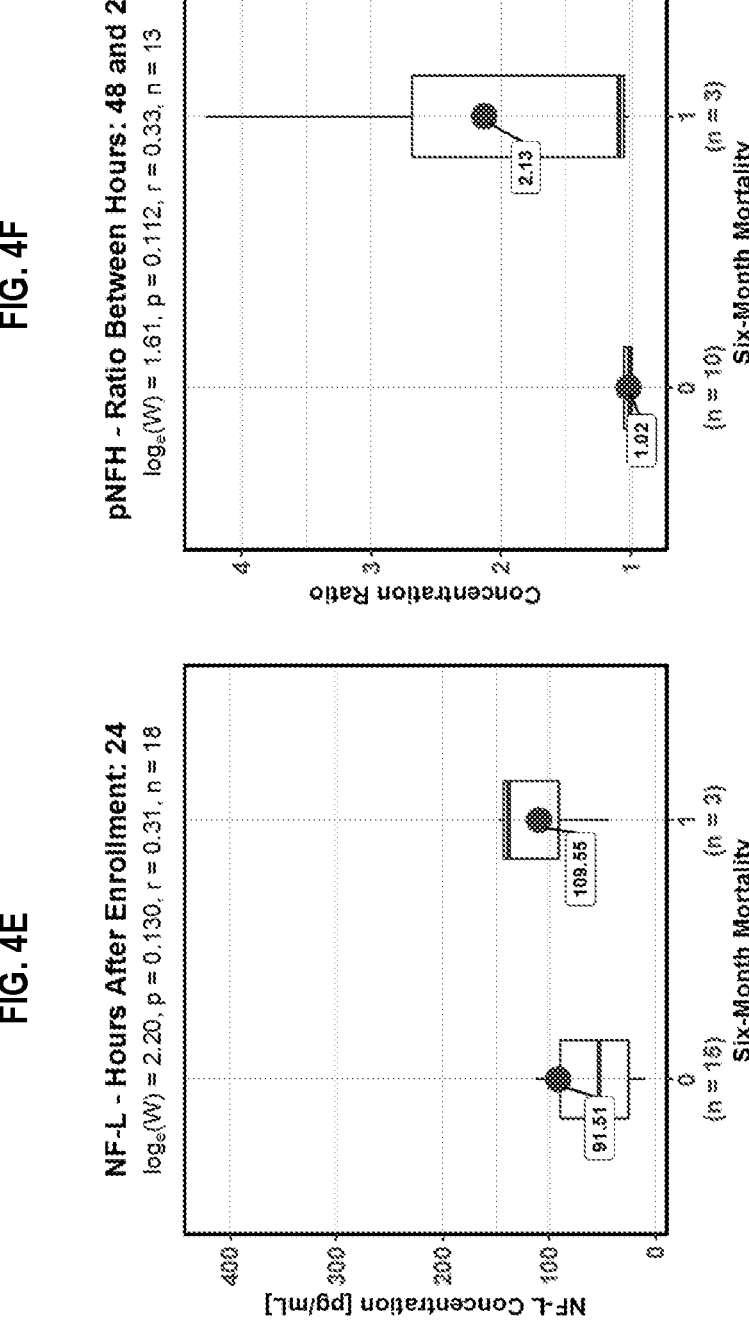
Figures 4G, 4H:
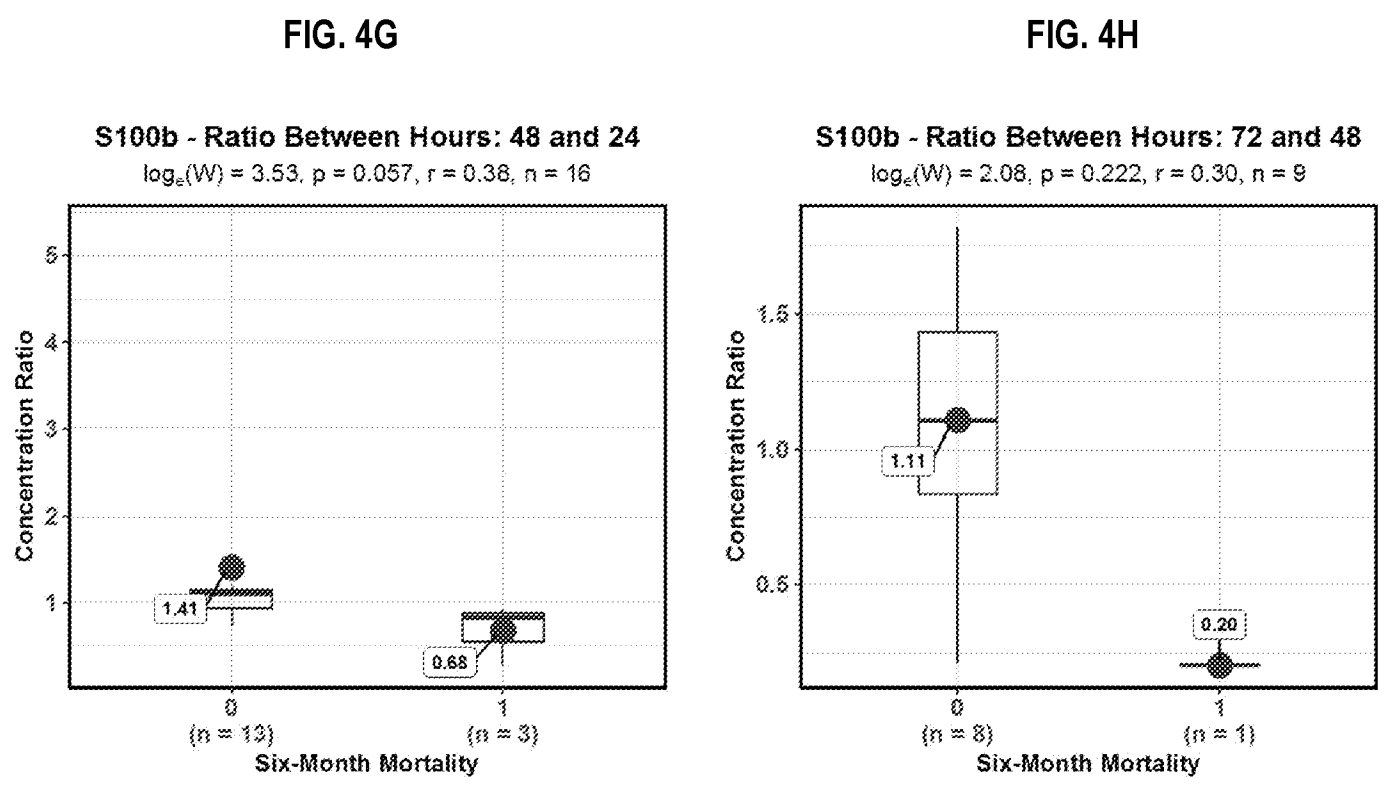
Figure 4J:
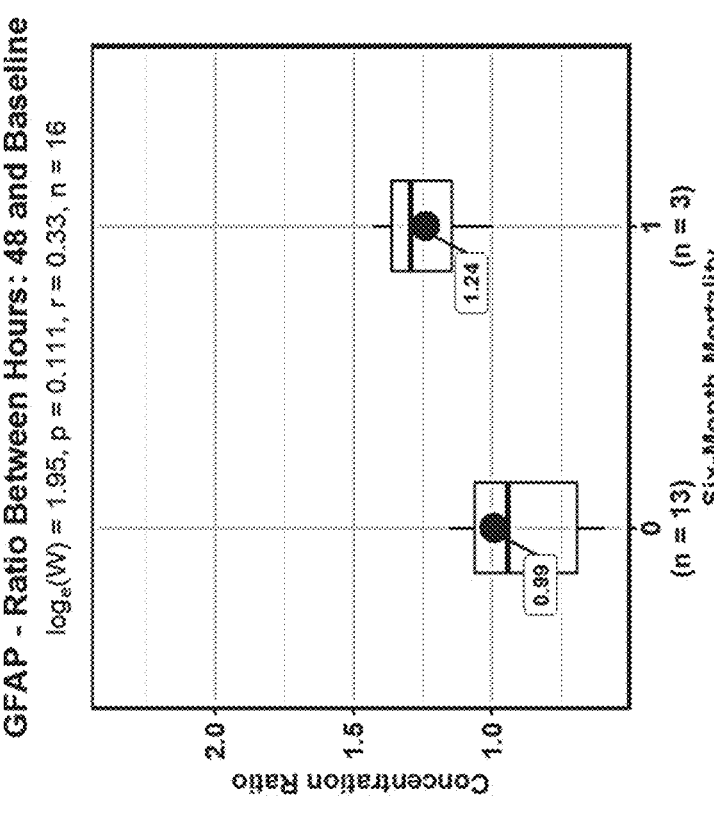
Figure 4I:
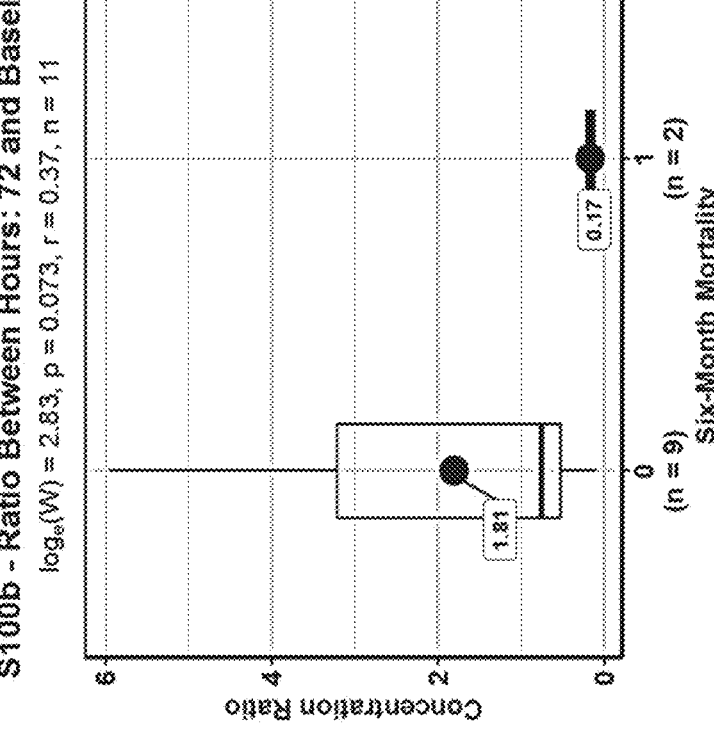
Figures 4K, 4L:
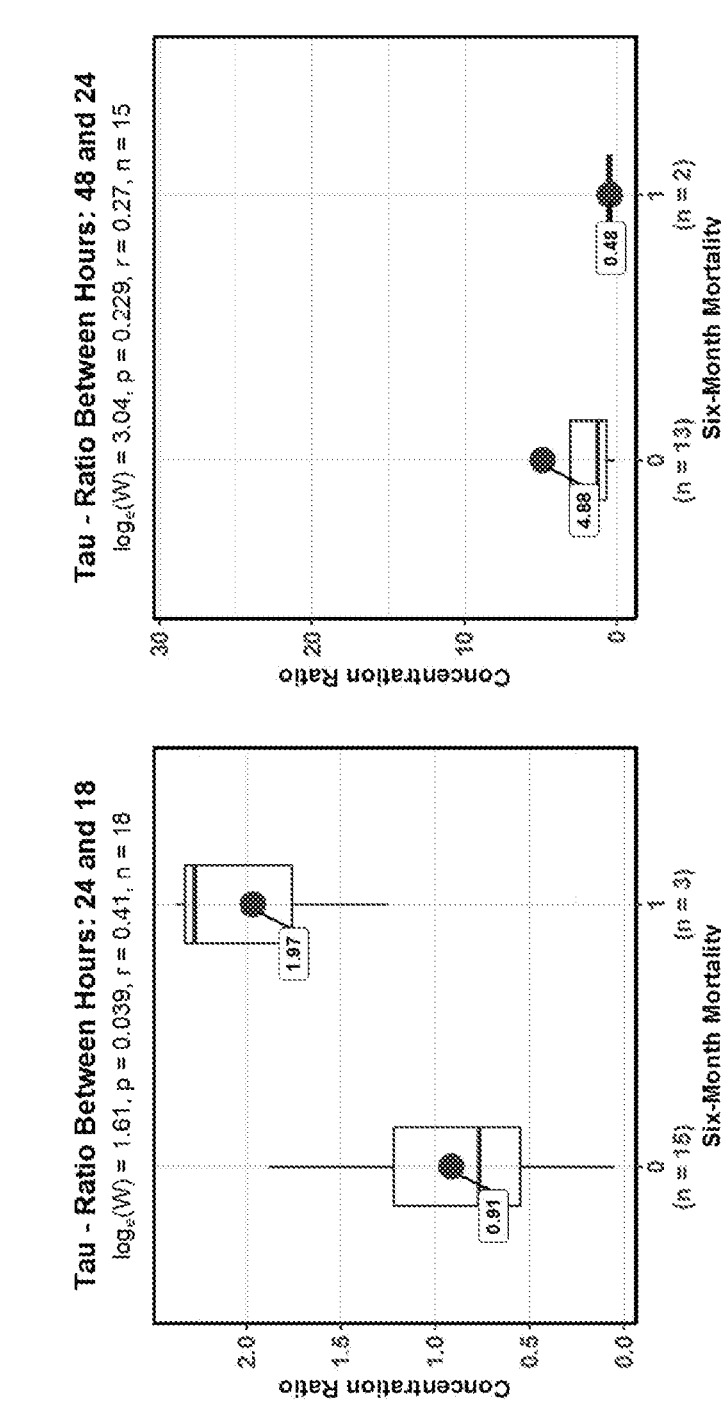

FIG. 4 presents the corresponding boxplots for the receiver-operating characteristic analysis in Tables 7 and 8, including FIG. 4A (Prognostic—Six-Month Mortality—Concentration—pNFH at Baseline), FIG. 4B (Prognostic—Six-Month Mortality—Concentration—Tau at 24 Hours), FIG. 4C (Prognostic—Six-Month Mortality—Concentration—Tau at 72 Hours), FIG. 4D (Prognostic—Six-Month Mortality—Concentration—NF-L at 6 Hours), FIG. 4E (Prognostic—Six-Month Mortality—Concentration—NF-L at 12 Hours), FIG. 4F (Prognostic—Six-Month Mortality—Ratio—pNFH at 48 Hours and 24 Hours), FIG. 4G (Prognostic—Six-Month Mortality—Ratio—S100b at 48 Hours and 24 Hours), FIG. 4H (Prognostic—Six-Month Mortality—Ratio—S100b at 72 Hours and 48 Hours), FIG. 4I (Prognostic—Six-Month Mortality—Ratio—S100b at 72 Hours and Baseline), FIG. 4J (Prognostic—Six-Month Mortality—Ratio—GFAP at 48 Hours and Baseline), FIG. 4K (Prognostic—Six-Month Mortality—Ratio—Tau at 24 Hours and 18 Hours), FIG. 4L (Prognostic—Six-Month Mortality—Ratio—Tau at 48 Hours and 24 Hours), FIG. 4M (Prognostic—Six-Month Mortality—Ratio—NF-L at 72 Hours and 48 Hours), FIG. 4N (Prognostic—Six-Month Mortality—Ratio—NF-L at 12 Hours and Baseline), FIG. 4O (Prognostic—Six-Month Mortality—Ratio—NF-L at 24 Hours and Baseline), and FIG. 4P (Prognostic—Six-Month Mortality—Ratio—NF-L at 48 Hours and Baseline).

Figure 5:
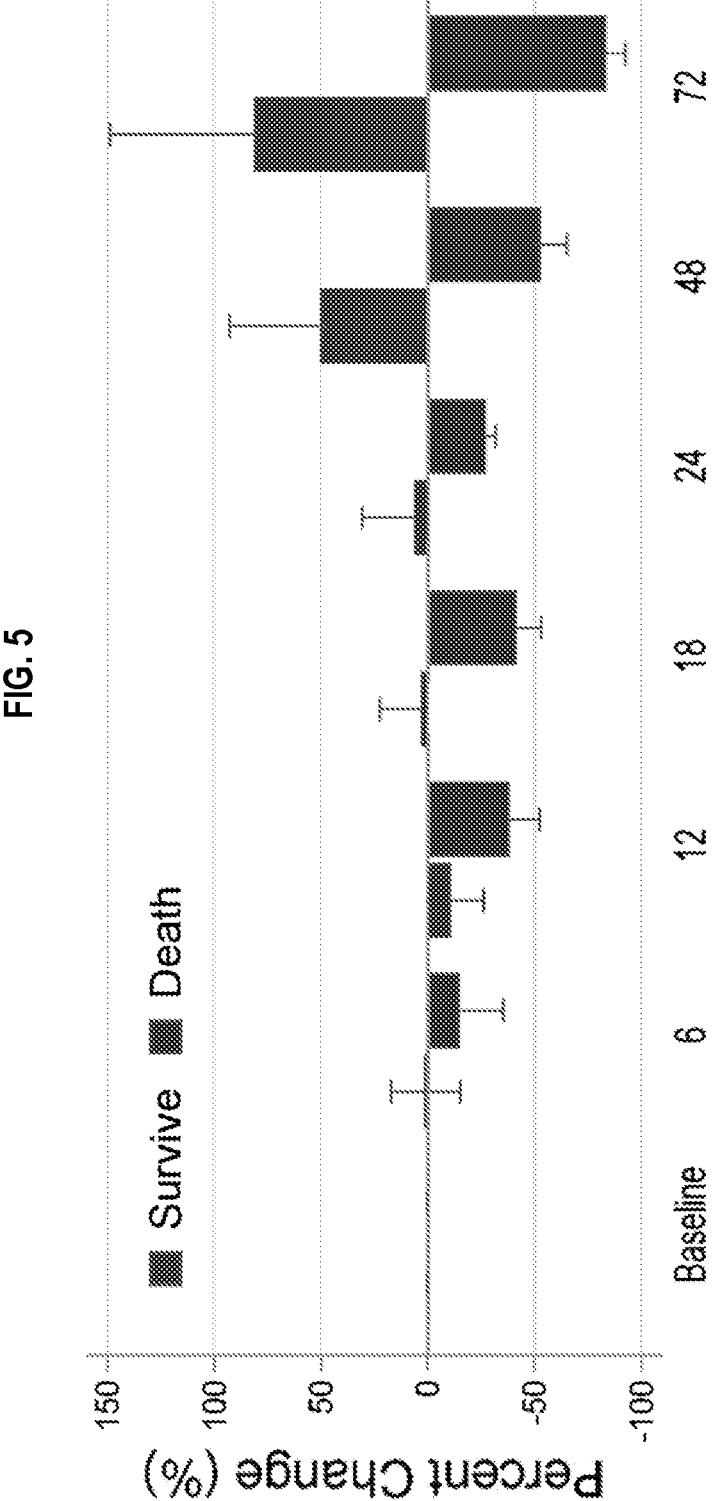

FIG. 5 is a bar graph showing the percent change in S100B from baseline at each study timepoint by 6-month mortality (p=0.007).

Figure 6:
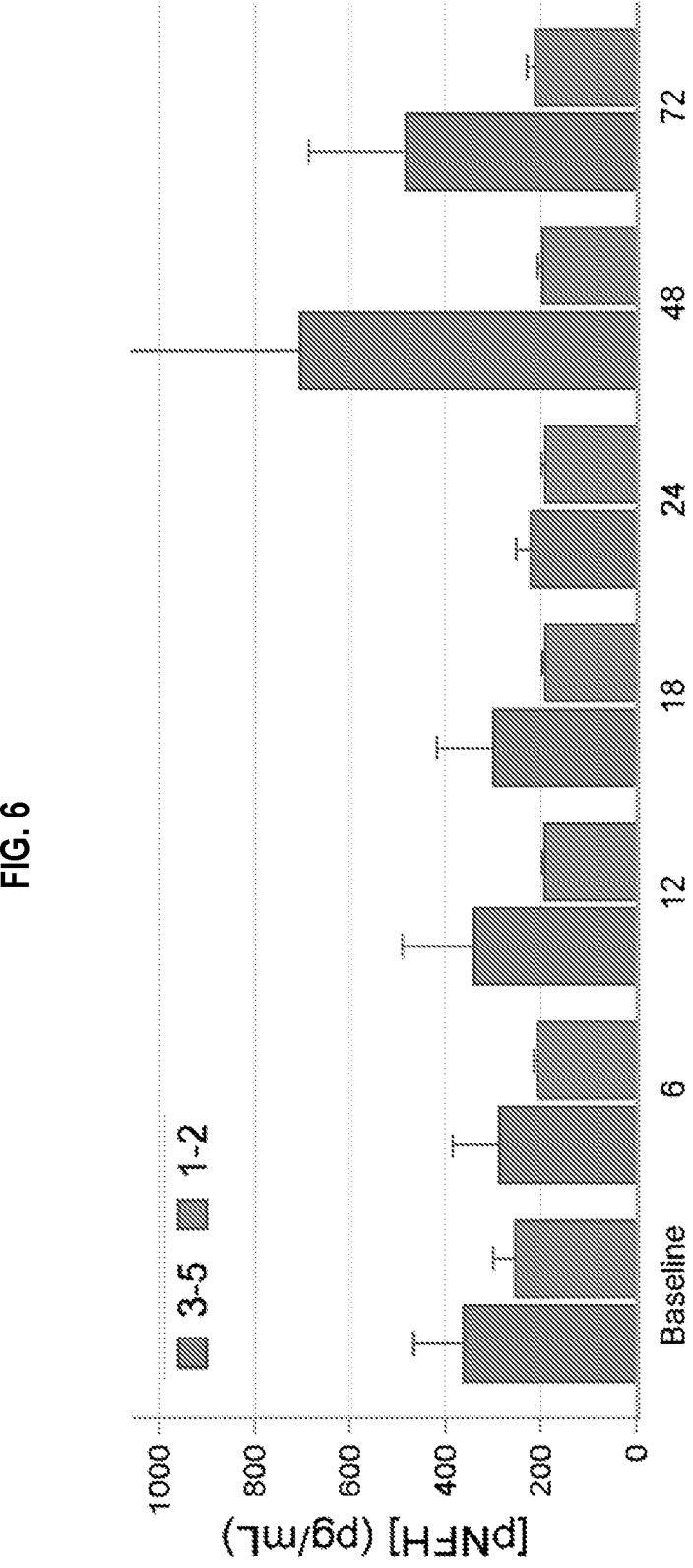

FIG. 6 is a bar graph showing the mean pNFH at each study timepoint by Cerebral Performance Category (CPC) score at discharge (p<0.001).

Figure 7:
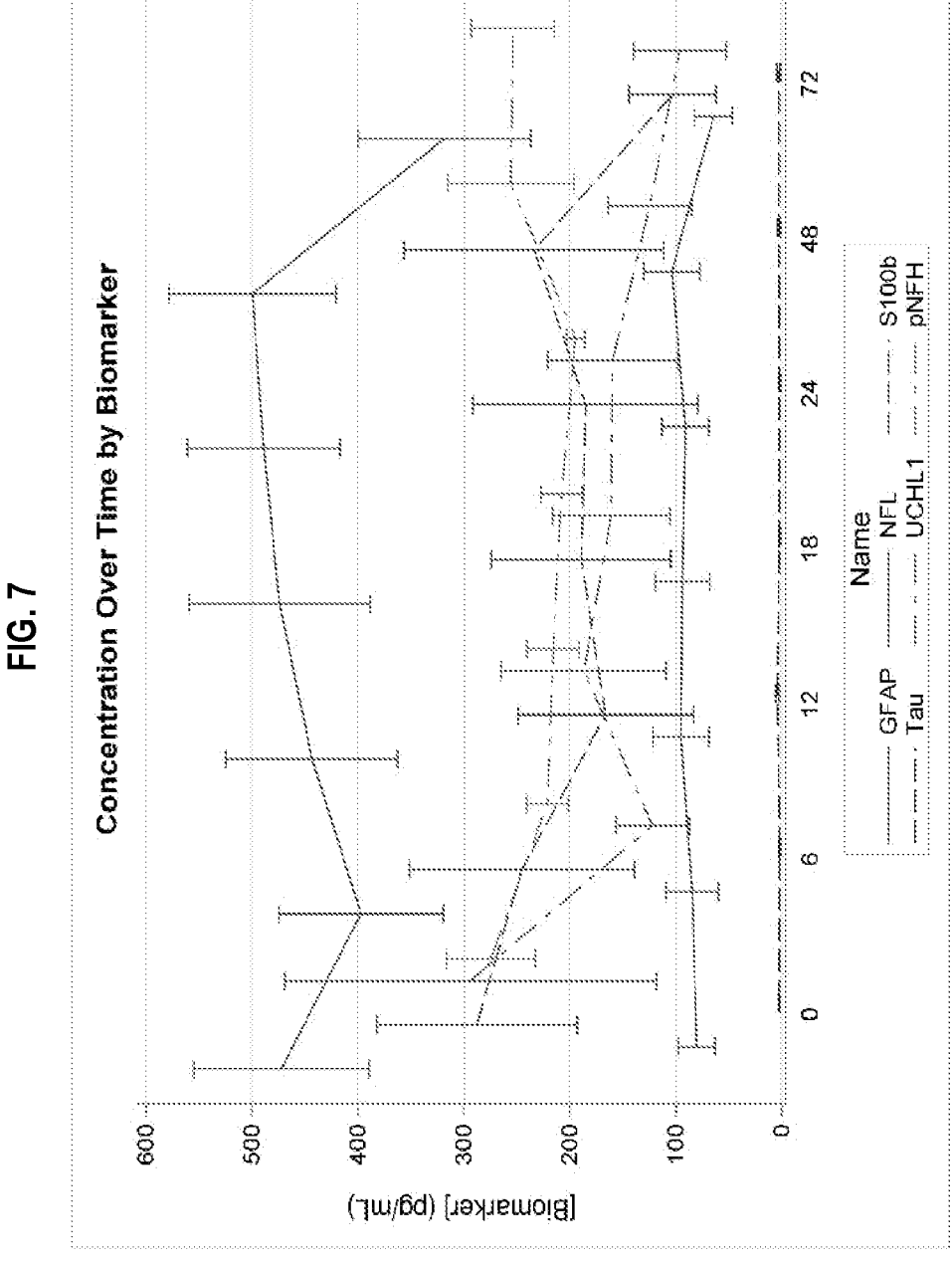

FIG. 7 shows the means±standard errors of aggregated biomarker concentrations for each study time point (hours from baseline).

Figure 8:
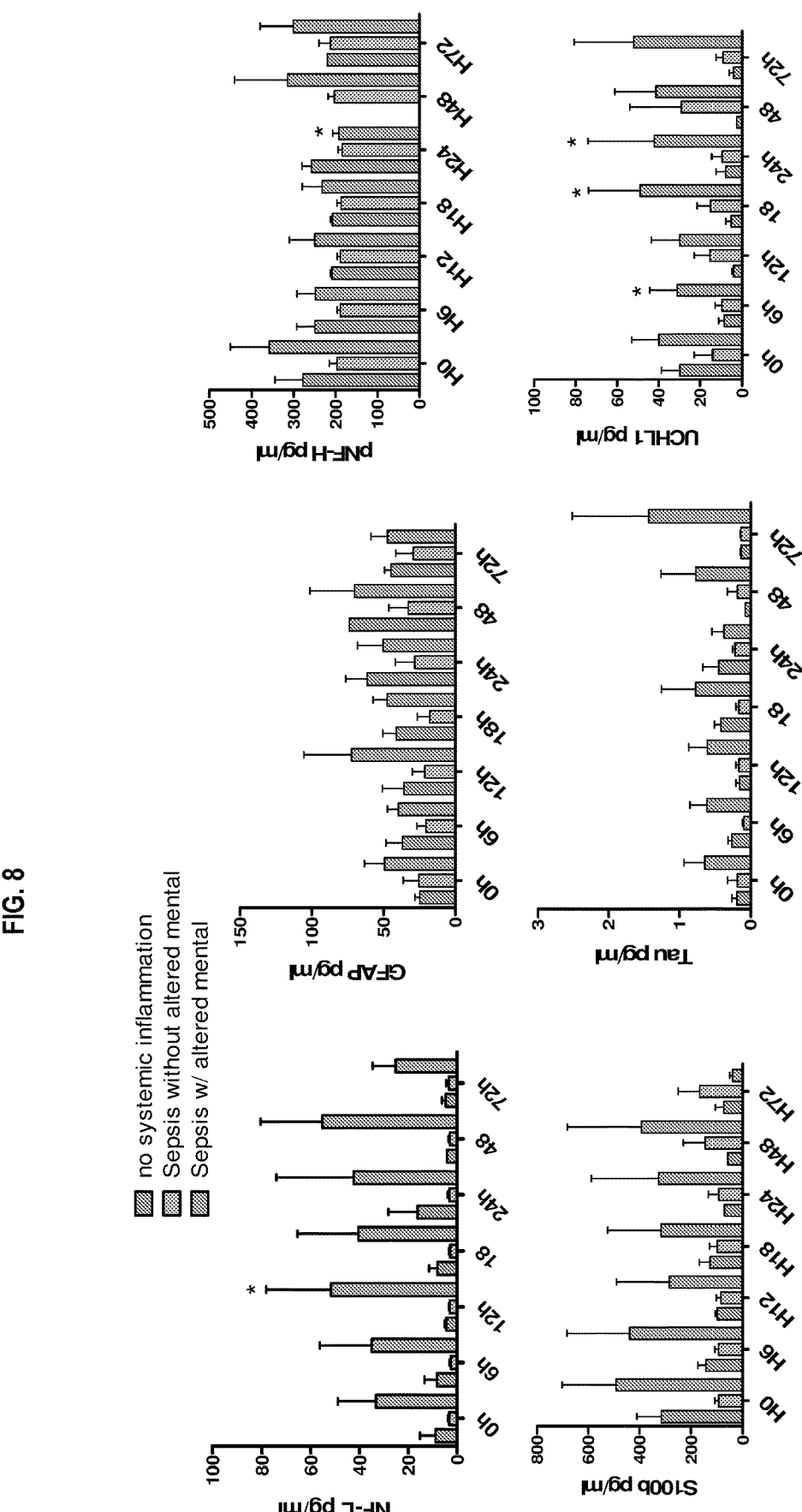

FIG. 8 shows that the mean and standard deviation of 6 brain biomarkers at different time points for sepsis patients with alerted mental status AMS (AMS), those without AMS and control subjects with no systemic inflammation. (*p, 0.05 unpaired T-test). Sepsis patients with AMS is generally regarded as SAE

DETAILED DESCRIPTION

1. Definitions

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

As used herein, the term "about," as used herein, means plus or minus 20 percent of the recited value, so that, for example, "about 0.125" means 0.125±0.025, and "about 1.0" means 1.0±0.2.

As used herein, the term "subject in need" advantageously refers to a mammal having SAE or suspected of having SAE, and also includes human patients who have or are suspected of having delirium or a disease or condition associated with critical illness. In particular, the conditions which a subject in need suffers from or is suspected of suffering from Sepsis or Critical Illness Associated Encephalopathy include, but are not limited to sepsis, shock, or other critical illness (a condition that threatens limb, organ, or life. The terms "patient" and "subject" are used interchangeably.

As used herein, the term "cerebral performance category (CPC)" score refers to a scale of 1 to 5 for grading general cerebral function. CPC 1: good cerebral performance; CPC 2: moderate cerebral disability; CPC 3: severe cerebral disability; CPC 4: coma or vegetative state; CPC 5: brain death.

As used herein, the term "diagnosis" and its cognates refers to determination or detection of whether a particular disease state or condition is present in a subject.

As used herein, the term "prognosis" and its cognates refers to the prediction or forecasting of symptoms, conditions, or survival associated with an illness or condition.

As used herein, the term "critical illness" refers to a condition which threatens the life, limb(s) or organ(s) of a patient. "Critical illness-related encephalopathies" refers to the state of impaired cognition manifested by confusion, hyperactive or hypoactive delirium, or change from the normal state of mentation in the setting of a limb, organ or life-threatening condition.

As used herein, the term "chronic cognitive failure" refers to the state of persistent deficit in thought or cognition for greater than 3 months.

As used herein, the term "cutpoint" refers to a value on an ordinal scale beyond which values are considered in the art to be clinically abnormal.

2. Overview

Protein fragments and/or peptides derived from glial fibrillary acidic protein (GFAP), S100 calcium-binding protein B (5-100B), ubiquitin C-terminal hydrolase L1 (UCH-L1), Tau protein, neurofilament light chain (NF-L), and phosphorylated neurofilament heavy chain (pNFH) have been identified as new sepsis-associated encephalopathy (SAE) biomarkers useful for diagnosis and prognosis of SAE and for management of patients suffering from SAE. Biofluid, preferably serum, samples from patients suffering from SAE or suspected of suffering from SAE can be tested for one or more of these biomarkers to obtain diagnostic or prognostic information.

3. Summary of Results

The diagnostic and prognostic utility of pNFH, S100B, UCHL-1, GFAP, pNFH, NF-L, and Tau protein, markers of neuronal body, axonal, and blood brain barrier integrity, were investigated to assess their role in predicting cognitive performance and outcomes in SAE. The results indicate that the acute presentation of SAE is associated with cognitive dysfunction at hospital discharge. The biomarkers tested here were able to discriminate between samples from patients demonstrating diagnosed acute SAE, and therefore can be useful to determine the prognosis for persistent cognitive dysfunction and long-term survival among sepsis patients. S100B, pNFH, GFAP, UCHL-1, Tau, and NF-L cutpoints have been identified to inform clinicians as to whether the subject's biomarker levels are abnormal, and how much so.

4. Embodiments of the Invention

A. Introduction

Using mass spectrometry and immunological methods, brain proteins from various CNS cell types (neuron, astrocyte, oligodendrocytes) are proteolytically broken down into protein fragments and small peptides in conditions of severe infection and sepsis of the brain or other structures in the cranium. These protein fragment and peptides are released from injured tissue into biofluids (such as blood, cerebrospinal fluid, and the like). Since these proteolytic events are brain injury-mediated, they represent specific candidates biomarkers for sepsis associated encephalopathy (SAE). The key sepsis associated encephalopathy biomarker panel include protein fragments and/or peptides derived from GFAP, 5-100B, UCHL-1, Tau protein, NF-L, and pNFH B. Study This single-center, prospective cohort study enrolled adult patients with suspected sepsis presenting to the University of Florida Health Emergency Department from Jun. 1, 2017 to MMM DD, 2019. The study protocol was approved by the University of Florida Institutional Review Board, and written informed consent was obtained for each patient or respective legal authorized representative before enrollment.

The study population included patients >18 years who presented to the emergency department with suspicion of infection and met Systemic Inflammatory Response Syndrome (SIRS) or quick Sequential Organ Failure (qSOFA) criteria at the time of enrollment. All subjects were enrolled within 6 hours of ED presentation. Exclusion criteria included (1) positive medical history of neurodegenerative disease, neurological disorder, psychiatric disease, hematological disorder, renal failure, or liver failure; (2) neurosurgery or acute brain injury within last 30 days; (3) active anemia at time of enrollment (hemoglobin<9 g/dL); (4) blood donation within the last 8 weeks; (5) pregnant or lactating female; (6) incarcerated; or (7) poor probability of survival to 6 months.

Initial patient eligibility screening was performed on all adult, patients presenting to the emergency department by formally trained study staff using defined inclusion criteria. Upon initial eligibility, a comprehensive secondary assessment was conducted by the study staff in the ED to ensure that each potential subject did not meet any exclusion definitions. Final determination of subject eligibility was conducted by the principal investigator.

Figure 1:
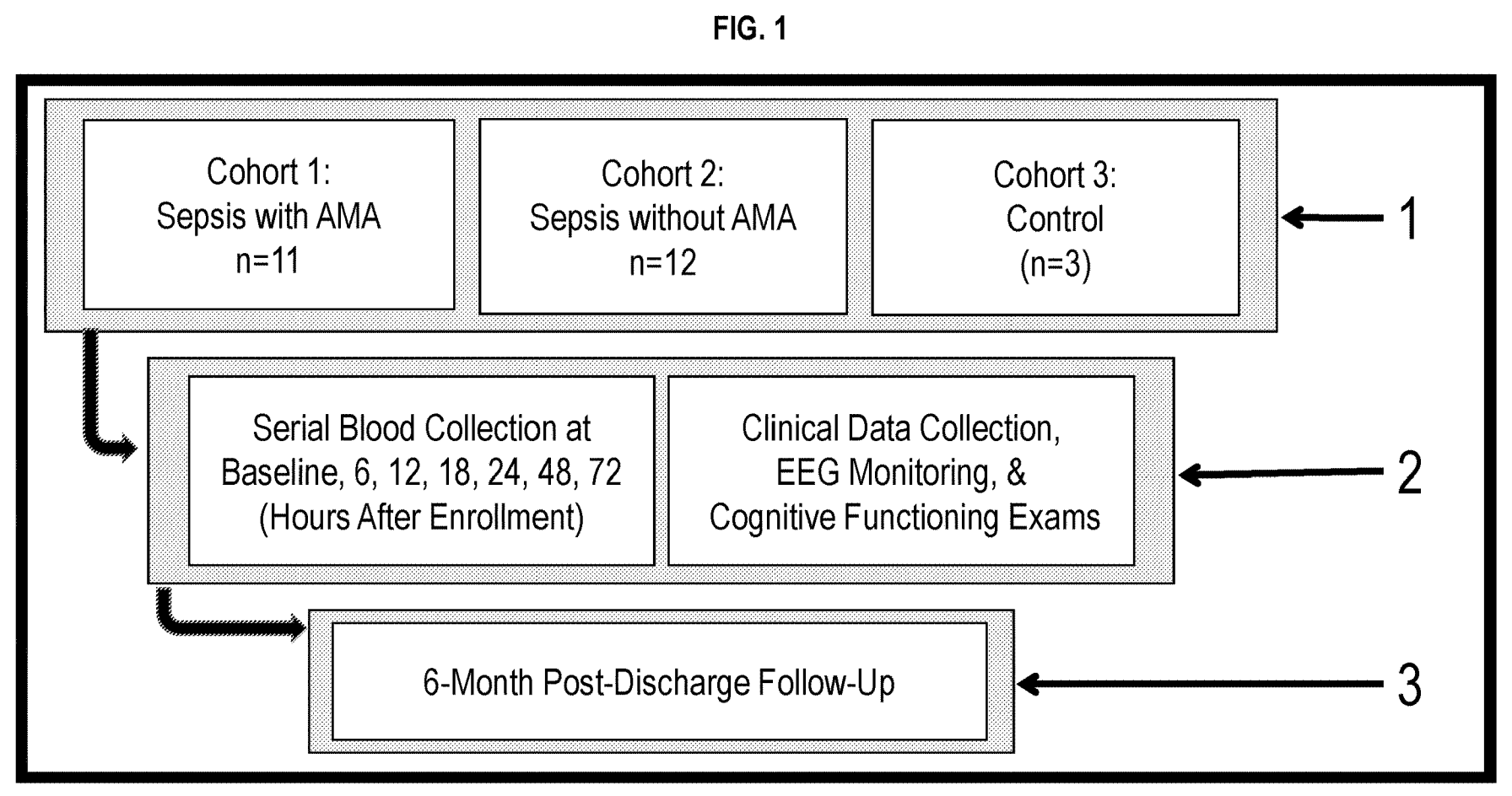

After consent, sub-cohort assignment and presence of altered mental status was defined a priori using Delirium Triage Screening (DTS), brief Confusion Assessment Method (bCAM), and board-certified emergency medicine physician. Sub-cohorts include (1) sepsis with altered mental status; (2) sepsis without altered mental status; and (3) control subject without any systemic inflammation. See FIG. 1, step 1. Baseline cognitive functioning status, clinical data, and blood samples were subsequently obtained. Repeated blood sampling was conducted at 6, 12, 18, 24, 48, and 72 hours (±30 minutes) after baseline sampling.

Cognitive function testing included a series of standardized surveys, including Short Blessed Test (SBT) and Cognitive Failures Questionnaire (CFQ), which measured the presence of altered mental status and cognitive status. DTS, bCAM, and SBT tests were continued for every 24 hours for 72 hours from baseline testing. Cerebral Performance Category (CPC) was performed at time of hospital discharge and at 6-month follow-up to measure functional neurological status. Clinical data, such as Glasgow Coma Scale (GCS), Sequential Organ Failure Assessment (SOFA), and Acute Physiology and Chronic Health Evaluation (APACHE II), was collected daily at time of cognitive testing. At six months after discharge, a follow-up, including Cognitive Failures Questionnaire (CFQ), was performed on each subject. See FIG. 1.

B. Subjects and Sampling

Blood samples for biomarker analysis consisted of approximately 10-20 mL of blood collected via venipuncture or IV, and placed in collection tubes with clot activator plugs. Collection tubes were allowed to clot at room temperature for up to 30 minutes to ensure sufficient coagulation. Samples were centrifuged at 1500×g for 5 minutes, and the resulting serum was placed in bar-coded aliquot containers and stored in a freezer at −80° C. until it was transported to a central laboratory. Alternatively, serum, plasma, or filtered whole blood samples can be obtained by any method known in the art for use with embodiments of the invention.

Advantageously, the subjects for which the invention can be useful include, but are not limited to any mammal, preferably a human patient, having SAE or suspected of having SAE, and also includes human patients who have or are suspected of having delirium or a disease or condition associated with critical illness. In particular, the conditions which a subject in need suffers from or is suspected of suffering from Sepsis or Critical Illness Associated Encephalopathy include, but are not limited to sepsis, shock, or other critical illness (a condition that threatens limb, organ, or life.

C. Markers

The biomarkers useful for the invention include the brain-originated and/or brain-enriched protein biomarkers Tau, NF-L, GFAP, S100B, UCHL-1, pNFH, neuron specific enolase (NSE), mature brain derived neurotrophic factor (BDNF), and Pro-BDNF (the proform of brain derived neurotrophic factor). These are either full length pro-form, processed or fragmented or truncated forms of the full length proteins. Additional biomarkers include myelin basic protein, secretoneurin, Copeptin, spectrin breakdown products (SBDP145, SBDP150), αII-spectrin N-terminal fragment, neuron specific enolase, brain derived neurotrophic factor, and full-length ProBDNF. The UniProtKB numbers for certain biomarkers (based on human proteins) are as follows: UCH-L1 (P09936), GFAP (P14136), NF-H/pNF-H (P12036), NF-L (P07196), Tau/MAPT (P10636), S100B (P04271), NSE (gamma-enolase/ENOG; P09104). αII-spectrin (SPTN1; Q13813), Secretogranin (SCG1 (P05060; SCG2 (P13521); SCG3 (Q8WXD2), and BDNF/Pro-BDNF (P2356).

D. Compositions and Kits

Compositions which are considered an embodiment of the invention include capture antibodies that specifically recognize the biomarkers to be detected and/or quantitated, and detection or secondary antibodies, ELISA plates, buffers, positive, negative controls, and kits for protein detection that can be used according to known methods to detect the biomarker proteins and peptides.

E. Methods

Protein biomarker immunoassay quantitation can be performed by any convenient method known to the person of skill in the art. In particular, brain-originated and/or brain-enriched protein biomarkers (Tau, NF-L, GFAP, UCHL-1, pNF-H, S100B, NSE, BDNF, Pro-BDNF) can be assayed in serum, plasma or filtered whole blood (25 to 100 microliter volume used) with commercial immunoassay kits (such as sandwich ELISA). General methods are as follows: Human Tau, NF-L, GFAP, UCHL-1 as multiplex (Quanterix™, Simoa Neuro™ 4-Plex A Advantage Kit item 102153) run on the as Quanterix™ SR-X equipment. Human S100B ELISA 96-Well Plate (Millipore™ Cat. #EZHS100B-33K), Human pNFH ELISA (BioVendor™, #RD191138300R), Mature brain derived neurotrophic factor (BDNF) (Biosensis™, #BEK-2211) and full-length ProBDNF (Biosensis™, #BEK-2217), and Human Neuron-specific enolase (NSE) (BioVendor™, #RIM002R) run on colorimetric sandwich ELISA platforms. Any convenient method known in the art is suitable, for example the methods described in Yang et al. Molecular Neurobiology 55(3):2174-2184, 2018; Korley et al., J. Neurotrauma, 2018, Jul. 23.e-published doi: 10.1089/neu.2017.5623), the disclosures of which are hereby incorporated by reference in their entirety.

Two or more of the biomarkers can be used together for the diagnosis of sepsis patients who might be at risk of or at the early stage of developing sepsis associated encephalopathy (SAE) from those that do no, so that early interventions can be provided. In addition, such biomarker pairs (or more than two) measured at baseline (about 6 hours from ED admission) or at 72 hours can predict or prognosticate whether a sepsis patient is likely to die or if a sepsis patient who survives is likely to have poor neurological outcome (for example in 6 months) (see Table 9).

In one example, the two marker pair can be, for example, GFAP and UCH-L1 both measured at 6 hour baseline after sepsis diagnosis, or NF-L and pNF-H both measured at 72 hours from sepsis diagnosis. Methods can be used to optimally combine the 24 hour or 72 hour levels of the markers to provide the best SAE diagnosis in terms of specificity and selectivity (see Table 9).

In another example, the two marker pairs are an unobvious combination as outcome prognosis tools (for example; GFAP and Tau) both measured at 6 hour after ED admission or GFAP and S100B both measured at 72 hours from ED admission. Methods can be used to combine the 24 hour or 72 hour levels of the two selected biomarker to predict or prognosticate if a sepsis patient is likely to die or if a sepsis patient who survives but is likely to have poor neurological outcome (at discharge) or not (see Table 9, 10).

The relative change (increase or decrease) of a one or more biomarkers measured at least two time points following ED admission (e.g., 6 hours and 72 hours) or the ratio of the two measurements at two different time points can be used to develop an algorithm or other method for the diagnosis of the sepsis patients who might be at risk of or at the early stage of developing SAE from those that do not, so that early interventions can be provided (see Table 9). In addition, the invention can be used to measure the change of biomarker level so the ratio of two timed measurement can be used to predict or prognosticate if a sepsis patient is likely to die or whether a sepsis patient who survives is likely to have poor neurological outcome (for example in 3-6 months) (see Table 6-8).

In an example, we will measure one or more markers at least two time points following sepsis diagnosis. The relative change (increase or decrease) of a biomarker's levels or the ratio of the two measurements at two different time points can be used to develop an algorithm to inform on or diagnose the likelihood of the sepsis patients who are at risk of or at the early stage of developing sepsis associated encephalopathy (SAE) from those that do not (see Table 6-8).

In another example, we will measure one or more markers at least two time points following ED admission (e.g. 6 hours, 12 hours, 24 hours, 48 hours and 72 hours). The relative change (increase or decrease) of a biomarker's levels or the ratio of the two measurements at two different time points can be used to predict or prognosticate whether a sepsis patient is likely to die (in 6 month) or whether a sepsis patient who survives is likely to have poor neurological outcome at discharge (see Tables 6-8).

5. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

Example 1: S100B and pNFH Detect and Prognosticate Cognitive Failure and Mortality in Sepsis A single center, prospective, longitudinal study of ED patients over 18 years of age with suspected or confirmed infection and systemic inflammatory response syndrome (SIRS) criteria was performed (IRB: 201700135). Patients with a past medical history of neurodegenerative disease, acute brain injury, renal failure, liver failure, or severe anemia were excluded from the study. Subjects were recruited into one of three cohorts: (1) Sepsis with AMS, (2) Sepsis without AMS, and (3) Control (no systemic inflammation). AMS was determined a priori by the treating clinician and serial serum collection for biomarker analysis was performed 0, 6, 12, 18, 24, 48, and 72 hours after enrollment.

Figures 2A, 2B:
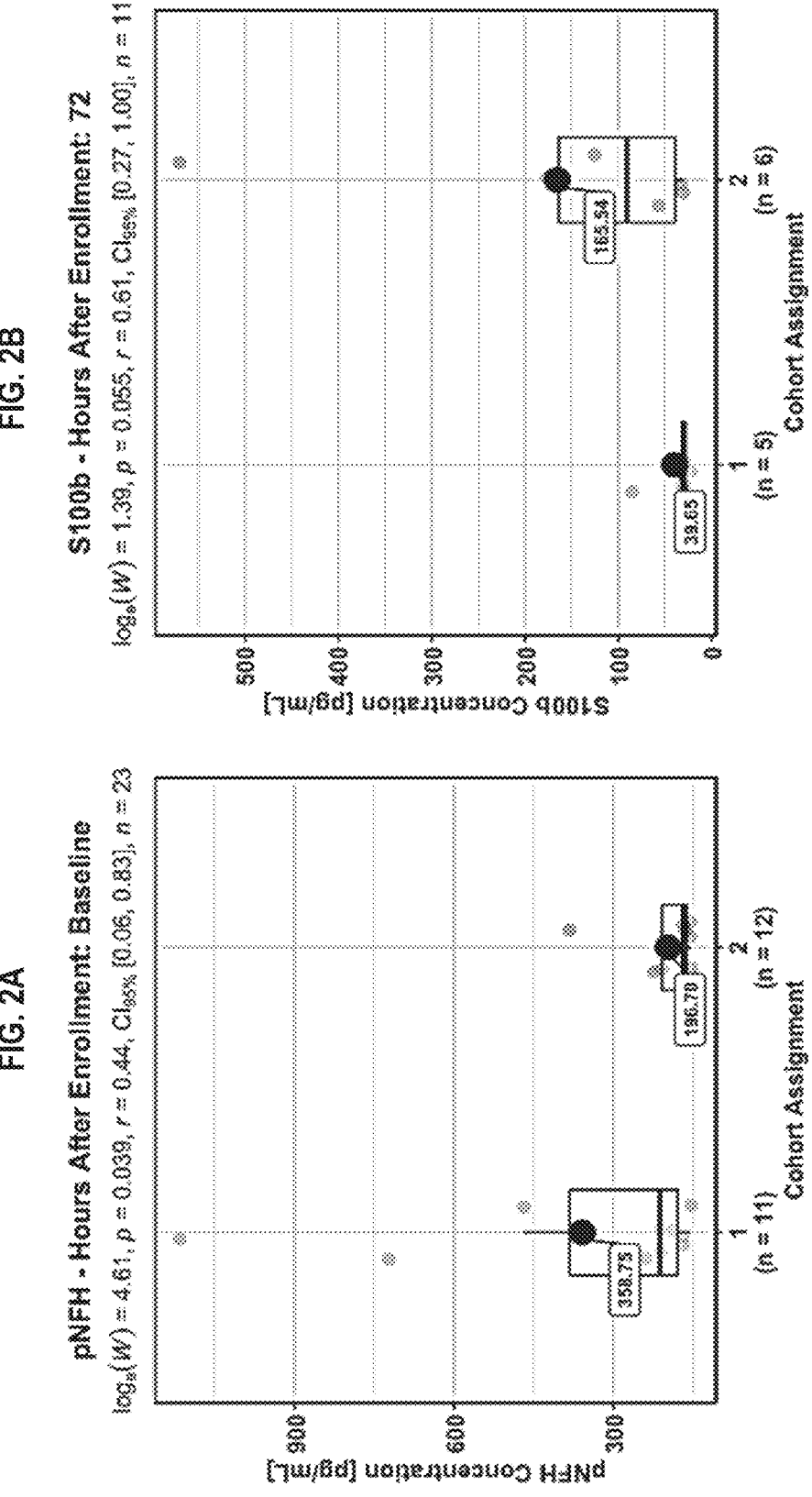
FIG. 2 presents the corresponding boxplots for the receiver-operating characteristic analysis in Tables 3 and 4, including FIG. 2A (Diagnostic—Sepsis Associated Encephalopathy—Concentration—pNFH at Baseline), FIG. 2B (Diagnostic—Sepsis Associated Encephalopathy—Concentration—S100b at 72 Hours), FIG. 2C (Diagnostic—Sepsis Associated Encephalopathy—Concentration—UCHL-1 at Baseline), FIG. 2D (Diagnostic—Sepsis Associated Encephalopathy—Concentration—UCHL-1 at 6 Hours), FIG. 2E (Diagnostic—Sepsis Associated Encephalopathy—Concentration—UCHL-1 at 12 Hours), FIG. 2F (Diagnostic—Sepsis Associated Encephalopathy—Concentration—UCHL-1 at 18 Hours), FIG. 2G (Diagnostic—Sepsis Associated Encephalopathy—Concentration—UCHL-1 at 24 Hours), FIG. 2H (Diagnostic—Sepsis Associated Encephalopathy—Concentration—UCHL-1 at 48 Hours), FIG. 2I (Diagnostic—Sepsis Associated Encephalopathy—Concentration—UCHL-1 at 72 Hours), FIG. 2J (Diagnostic—Sepsis Associated Encephalopathy—Ratio—pNFH at 24 and Baseline), FIG. 2K (Diagnostic—Sepsis Associated Encephalopathy—Ratio—pNFH at 72 and Baseline), FIG. 2L (Diagnostic—Sepsis Associated Encephalopathy—Ratio—S100b at 72 and Baseline), FIG. 2M (Diagnostic—Sepsis Associated Encephalopathy—Ratio—UCHL-1 at 24 and 18 Hours), FIG. 2N (Diagnostic—Sepsis Associated Encephalopathy—Ratio—GFAP at 18 and Baseline), FIG. 2O (Diagnostic—Sepsis Associated Encephalopathy—Ratio—GFAP at 24 and Baseline), FIG. 2P (Diagnostic—Sepsis Associated Encephalopathy—Ratio—GFAP at 48 and Baseline), FIG. 2Q (Diagnostic—Sepsis Associated Encephalopathy—Ratio—NF-L at 12 and Baseline), FIG. 2R (Diagnostic—Sepsis Associated Encephalopathy—Ratio—NF-L at 18 and Baseline), and FIG. 2S (Diagnostic—Sepsis Associated Encephalopathy—Ratio—NF-L at 24 and Baseline).
Figures 2C, 2D:
Figures 2E, 2F:
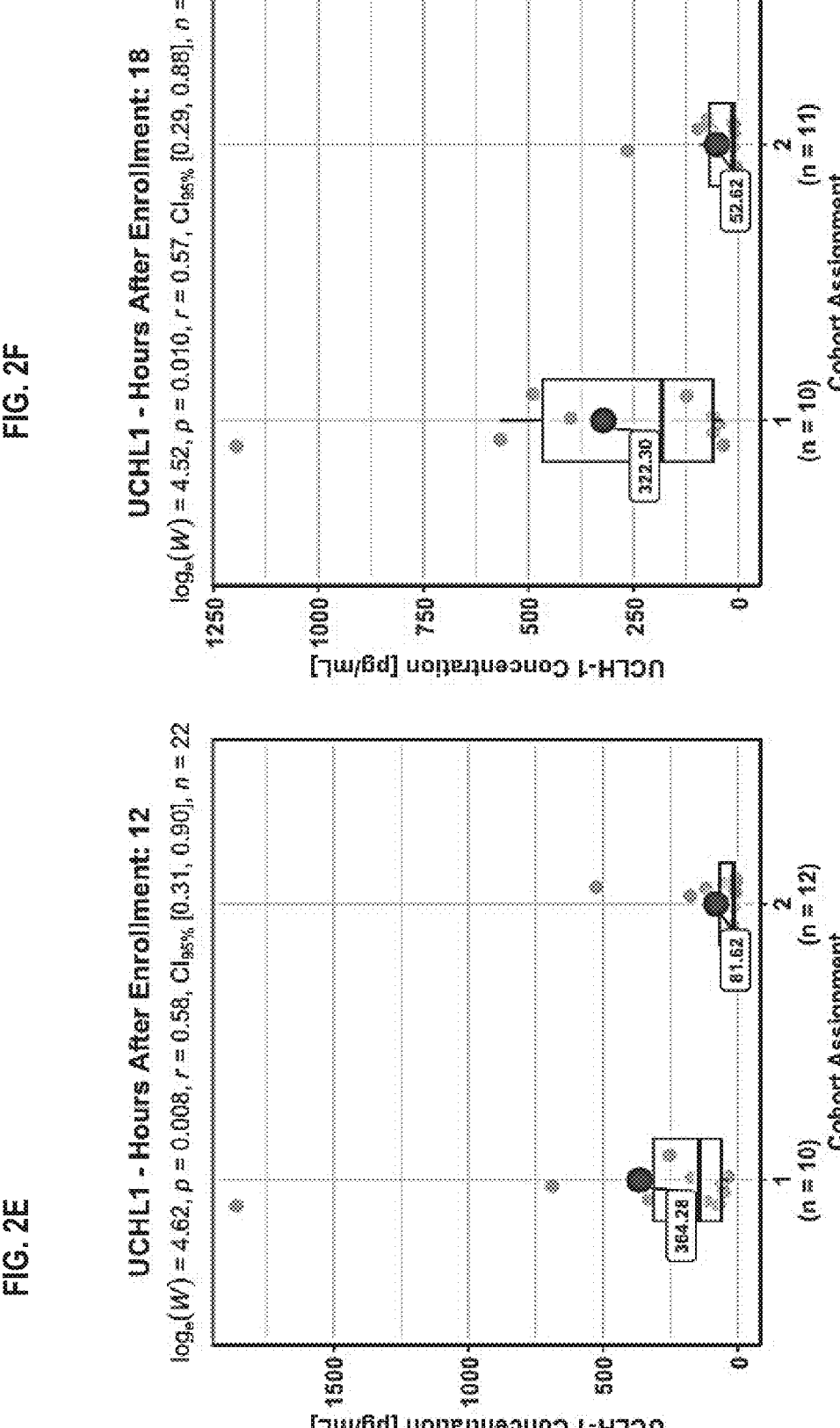
Figures 2G, 2H:
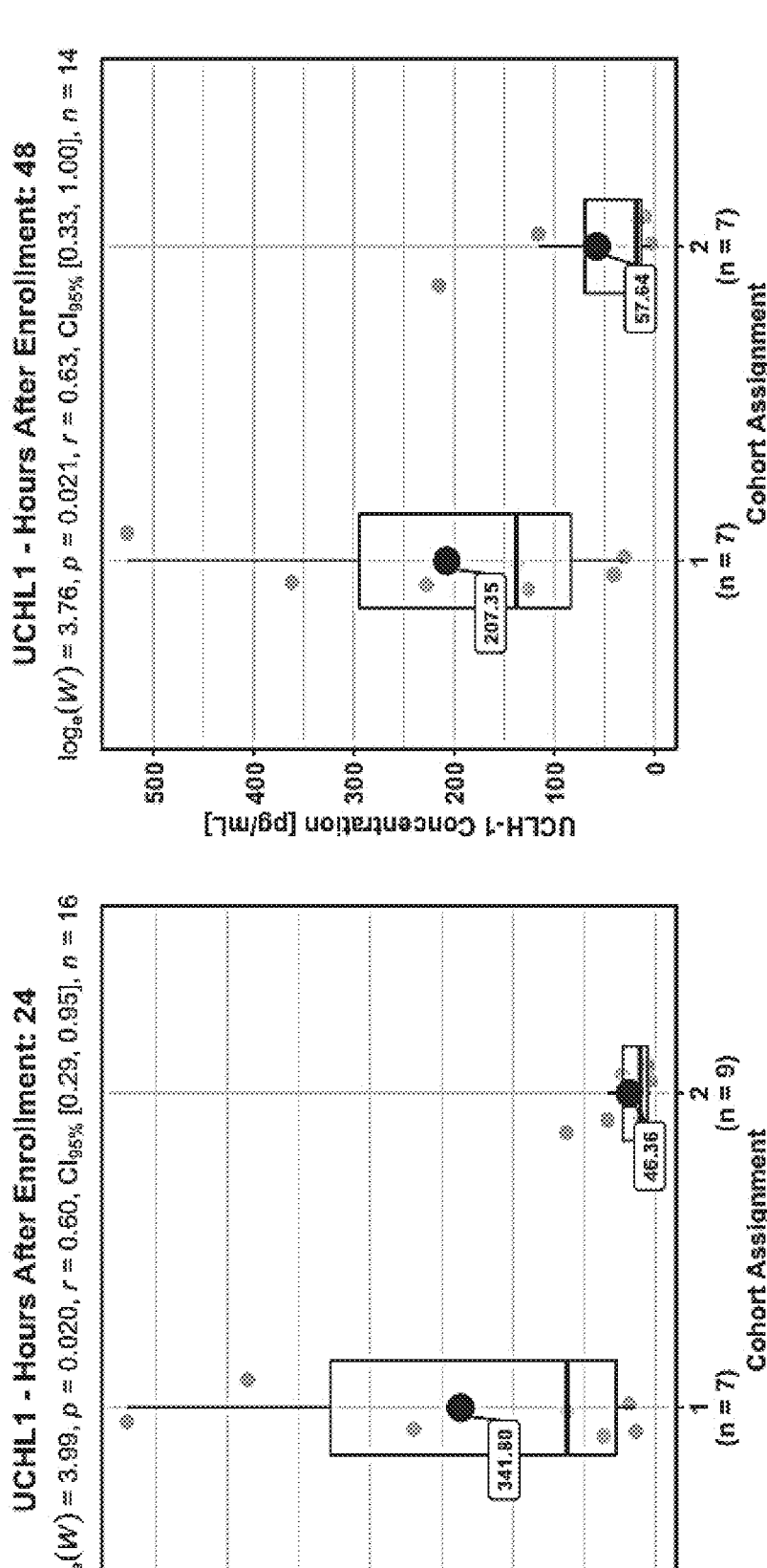
Figures 2I, 2J:
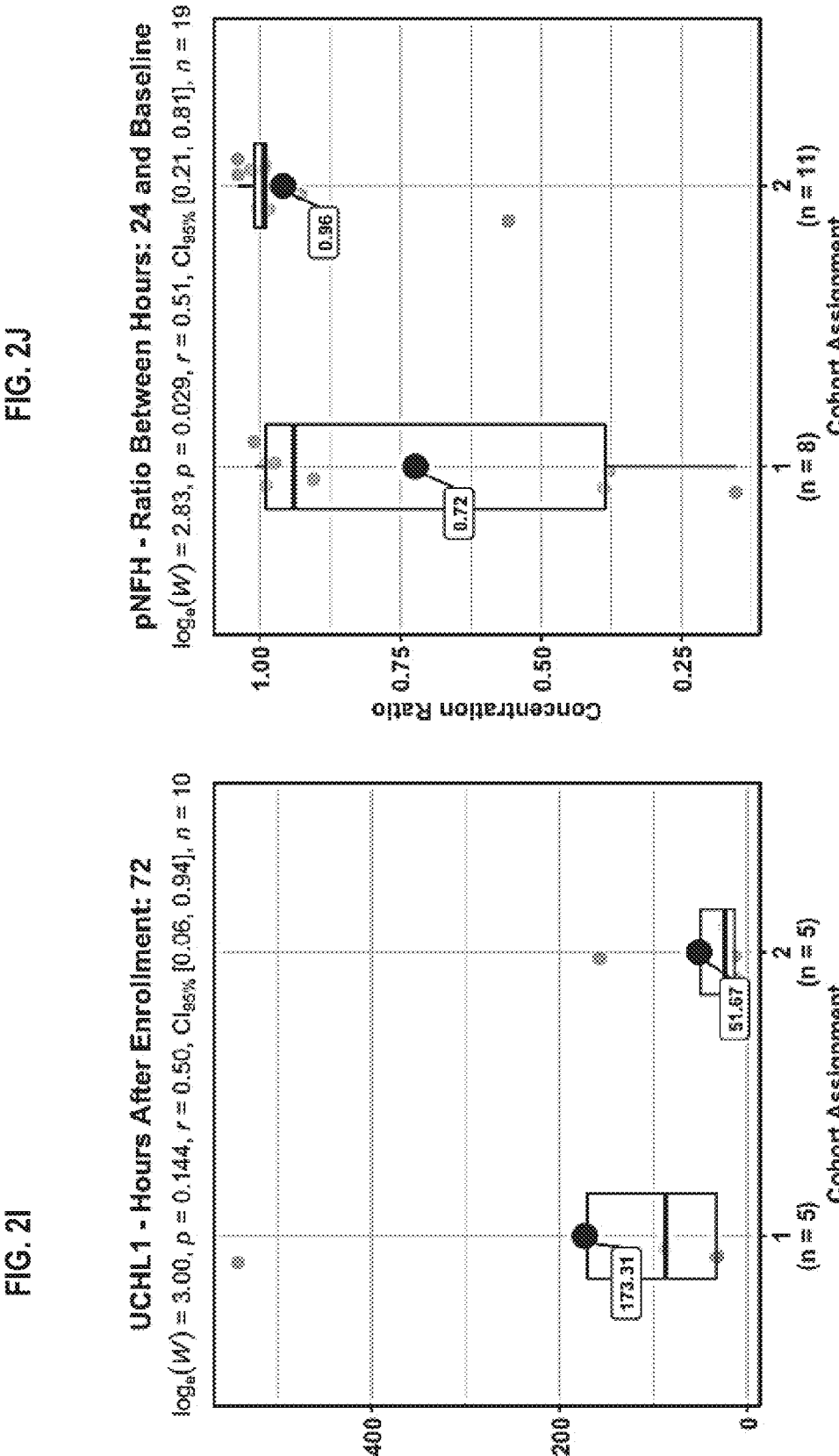
Figures 2K, 2L:
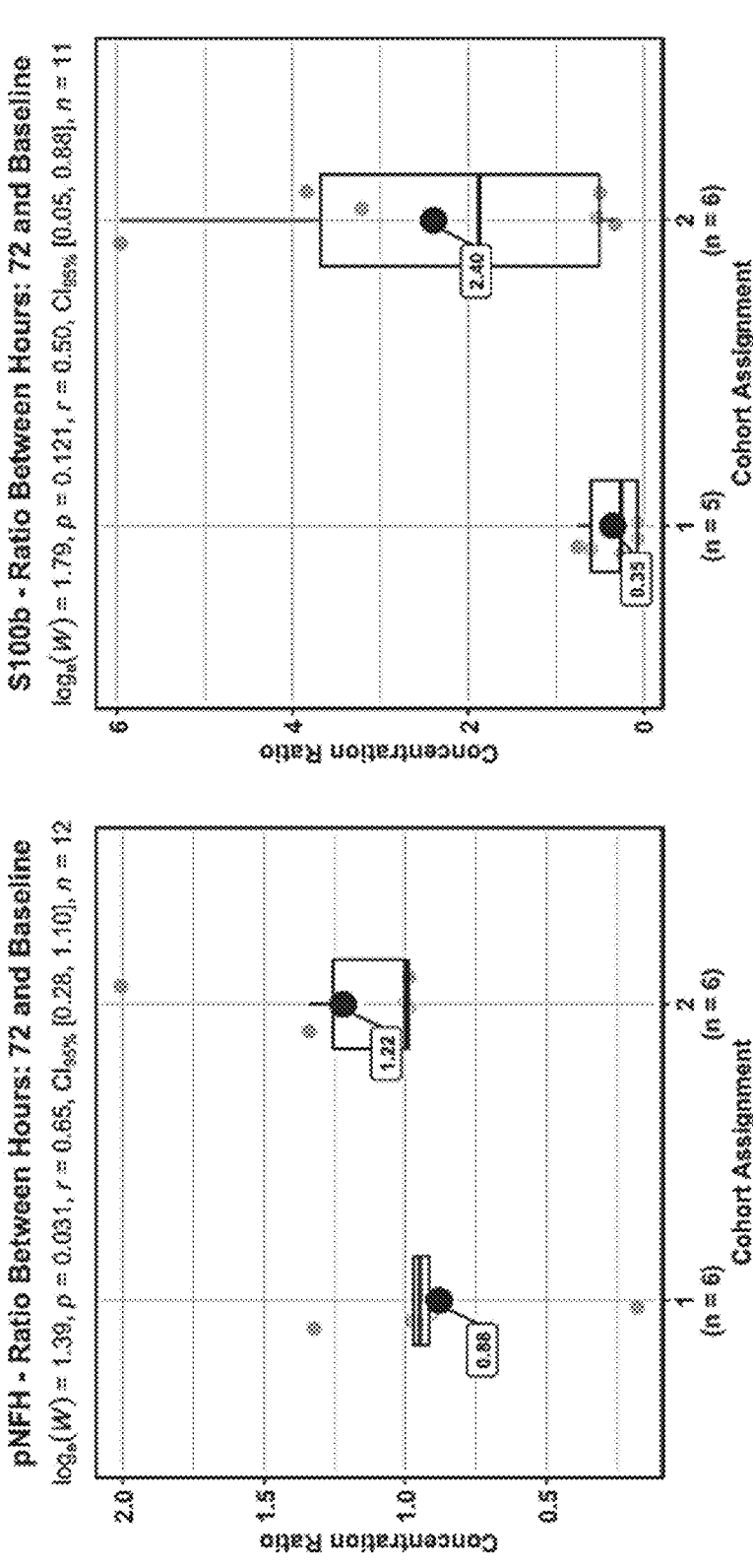
Figures 2M, 2N:
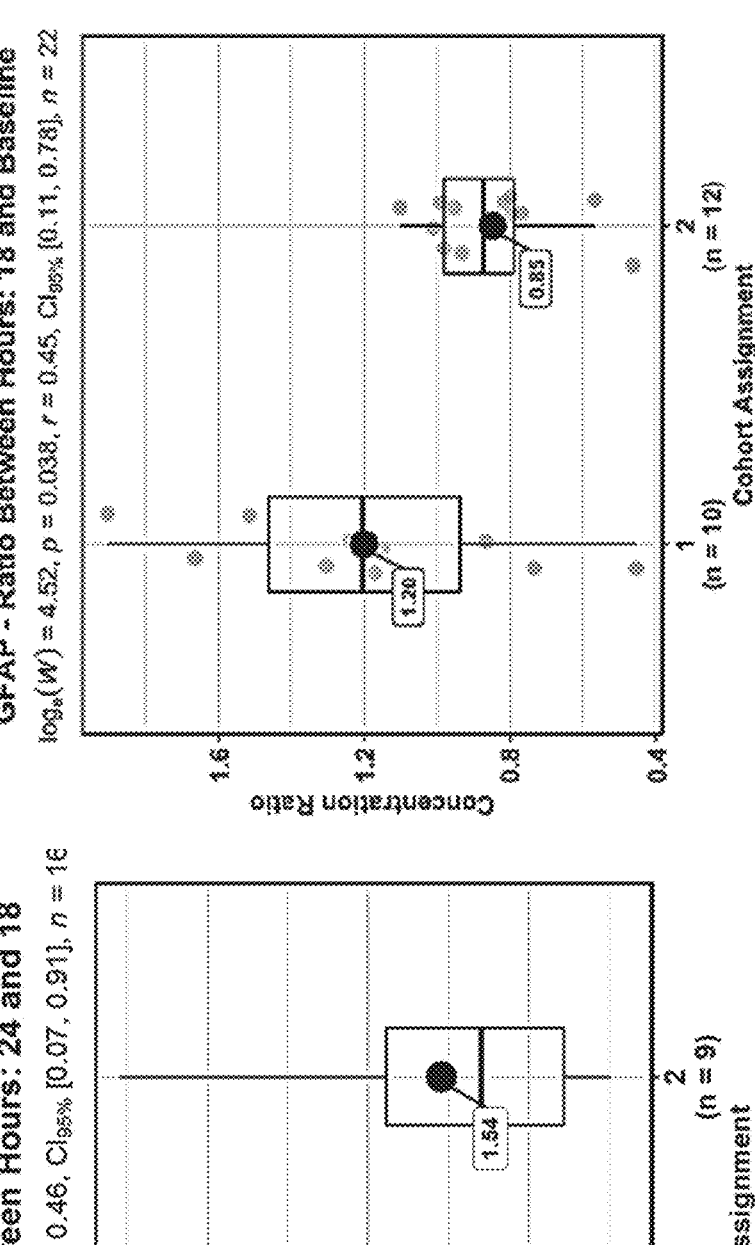
Figures 2O, 2P:
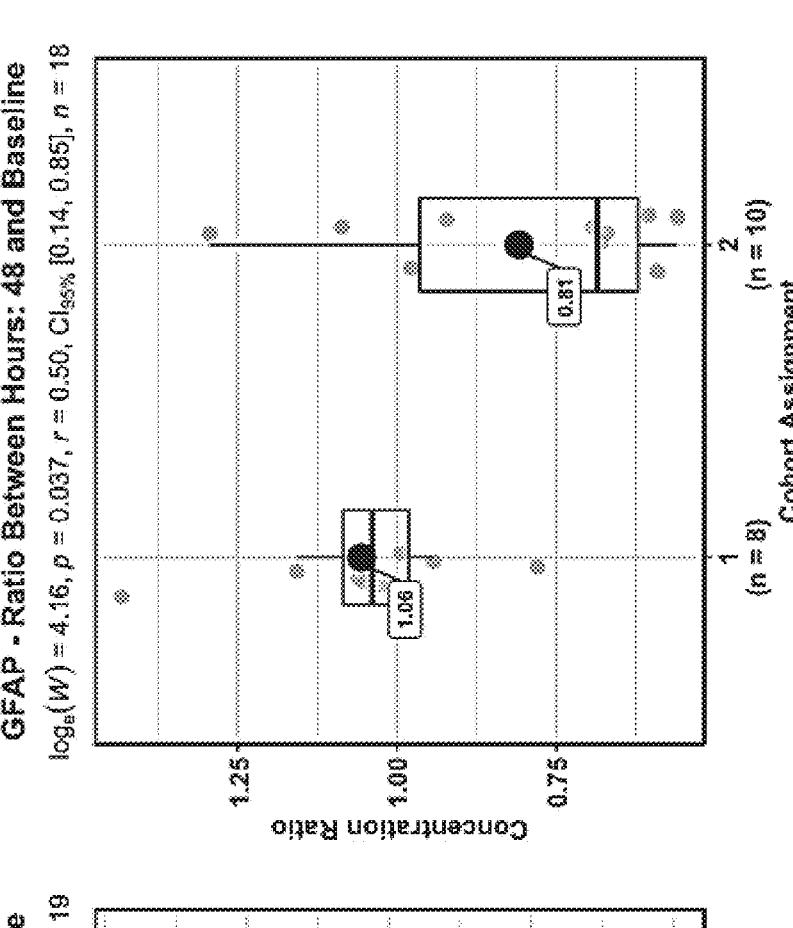
Figure 2R:
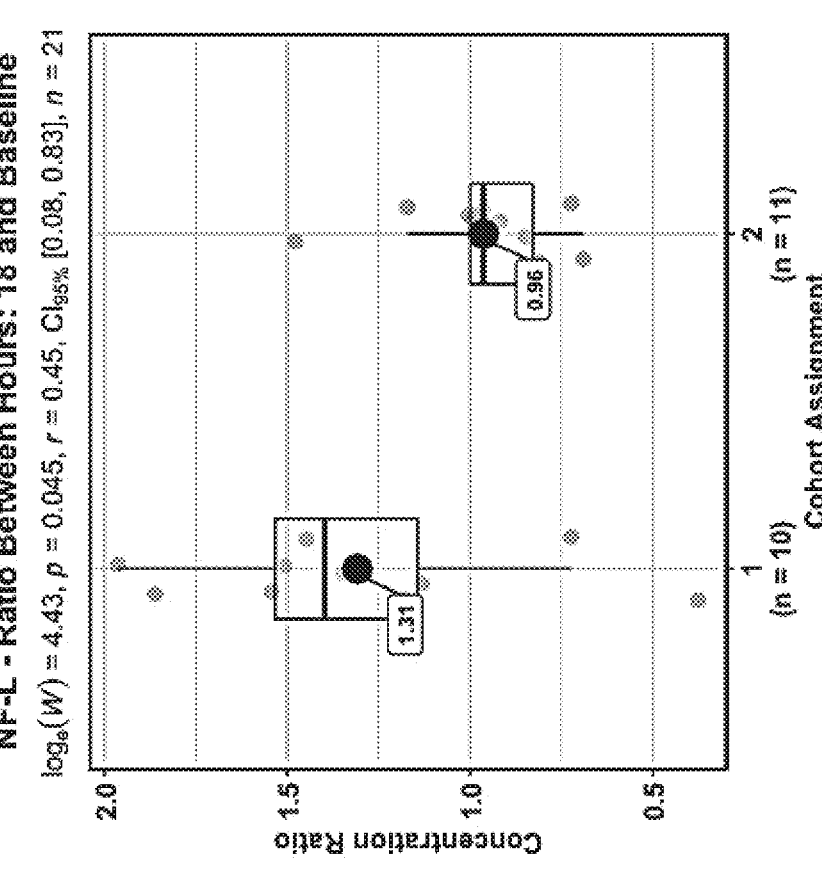
Figure 2Q:
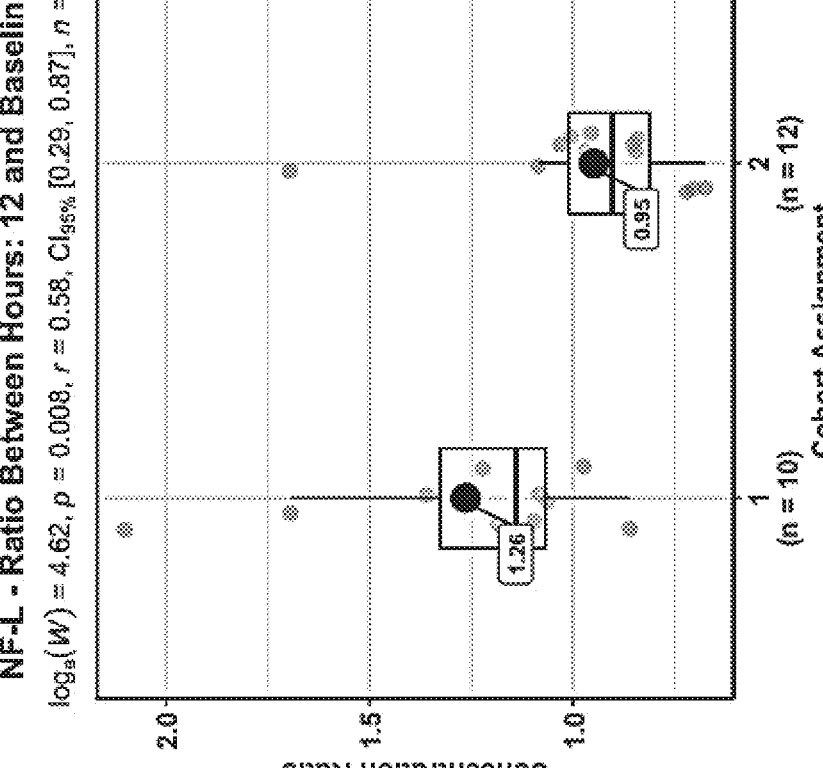
Figure 2S:
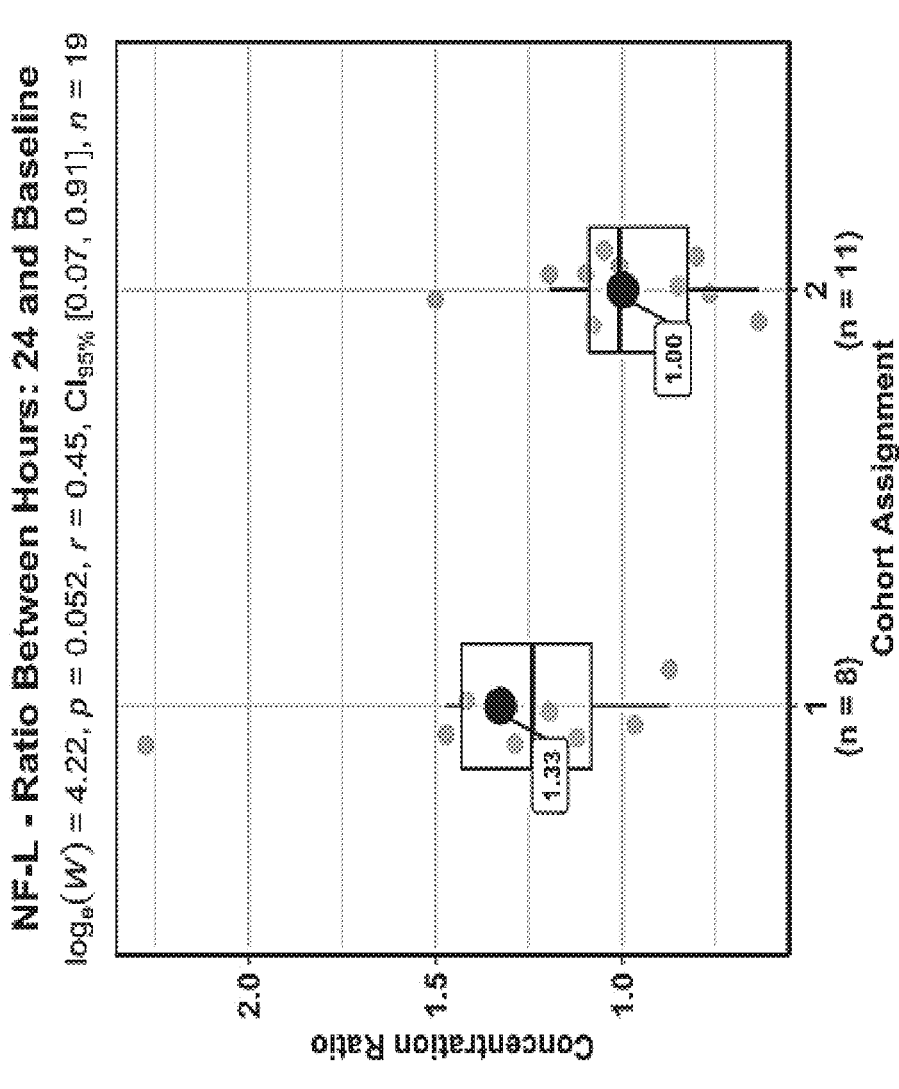
Figures 3E, 3F:
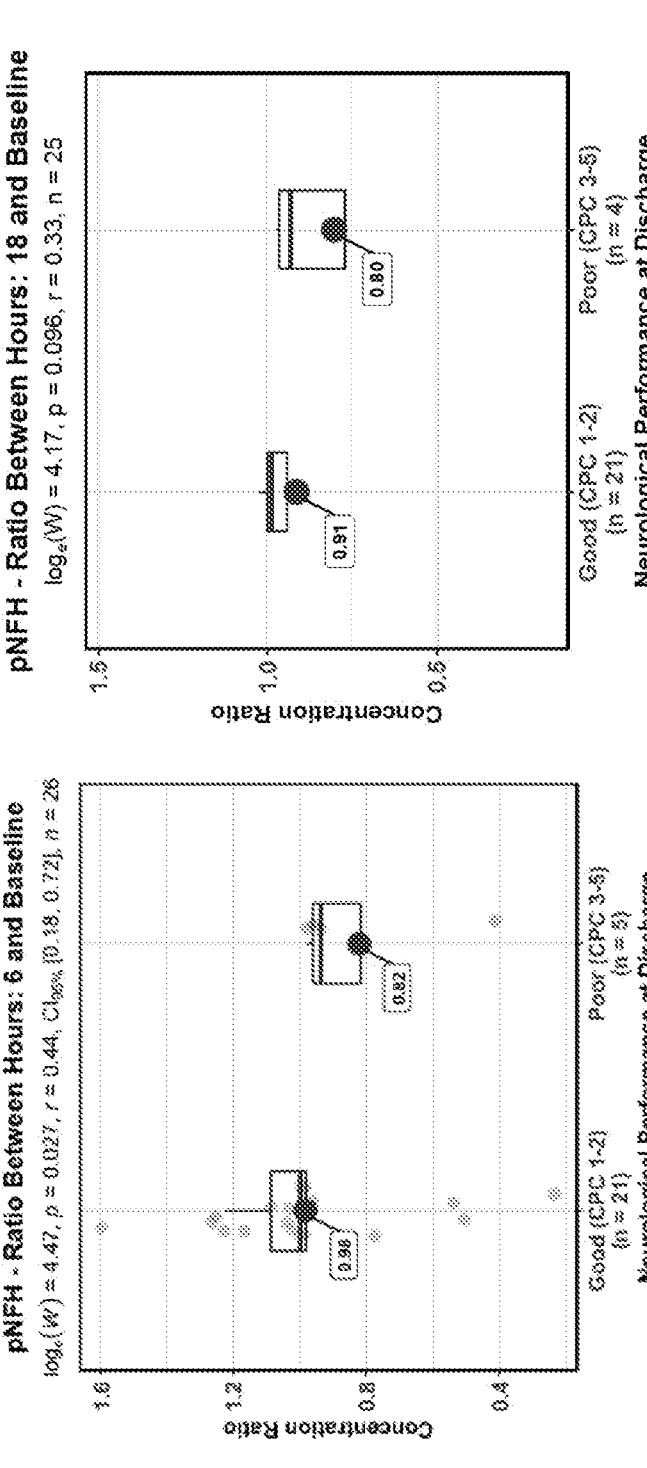
FIG. 3 presents the corresponding boxplots for the receiver-operating characteristic analysis in Tables 5 and 6, including FIG. 3A (Prognostic—Neurological Performance—Concentration—pNFH at Baseline), FIG. 3B (Prognostic—Neurological Performance—Concentration—pNFH at 48 Hours), FIG. 3C (Prognostic—Neurological Performance—Concentration—pNFH at 72 Hours), FIG. 3D (Prognostic—Neurological Performance—Concentration—Tau at 24 Hours), FIG. 3E (Prognostic—Neurological Performance—Ratio—pNFH at 6 Hours and Baseline), FIG. 3F (Prognostic—Neurological Performance—Ratio—pNFH at 18 Hours and Baseline), FIG. 3G (Prognostic—Neurological Performance—Ratio—pNFH at 24 Hours and Baseline), FIG. 3H (Prognostic—Neurological Performance—Ratio—S100b at 72 Hours and Baseline), FIG. 3I (Prognostic—Neurological Performance—Ratio—S100b at 72 Hours and 48 Hours), FIG. 3J (Prognostic—Neurological Performance—Ratio—UCHL-1 at 48 Hours and 24 Hours), FIG. 3K (Prognostic—Neurological Performance—Ratio—GFAP at 48 Hours and 24 Hours), FIG. 3L (Prognostic—Neurological Performance—Ratio—Tau at 24 Hours and 18 Hours), FIG. 3M (Prognostic—Neurological Performance—Ratio—Tau at 48 Hours and 24 Hours), FIG. 3N (Prognostic—Neurological Performance—Ratio—NF-L at 72 Hours and 48 Hours), FIG. 3O (Prognostic—Neurological Performance—Ratio—NF-L at 12 Hours and Baseline), and FIG. 3P (Prognostic—Neurological Performance—Ratio—NF-L at 24 Hours and Baseline).
Figures 3M, 3N:
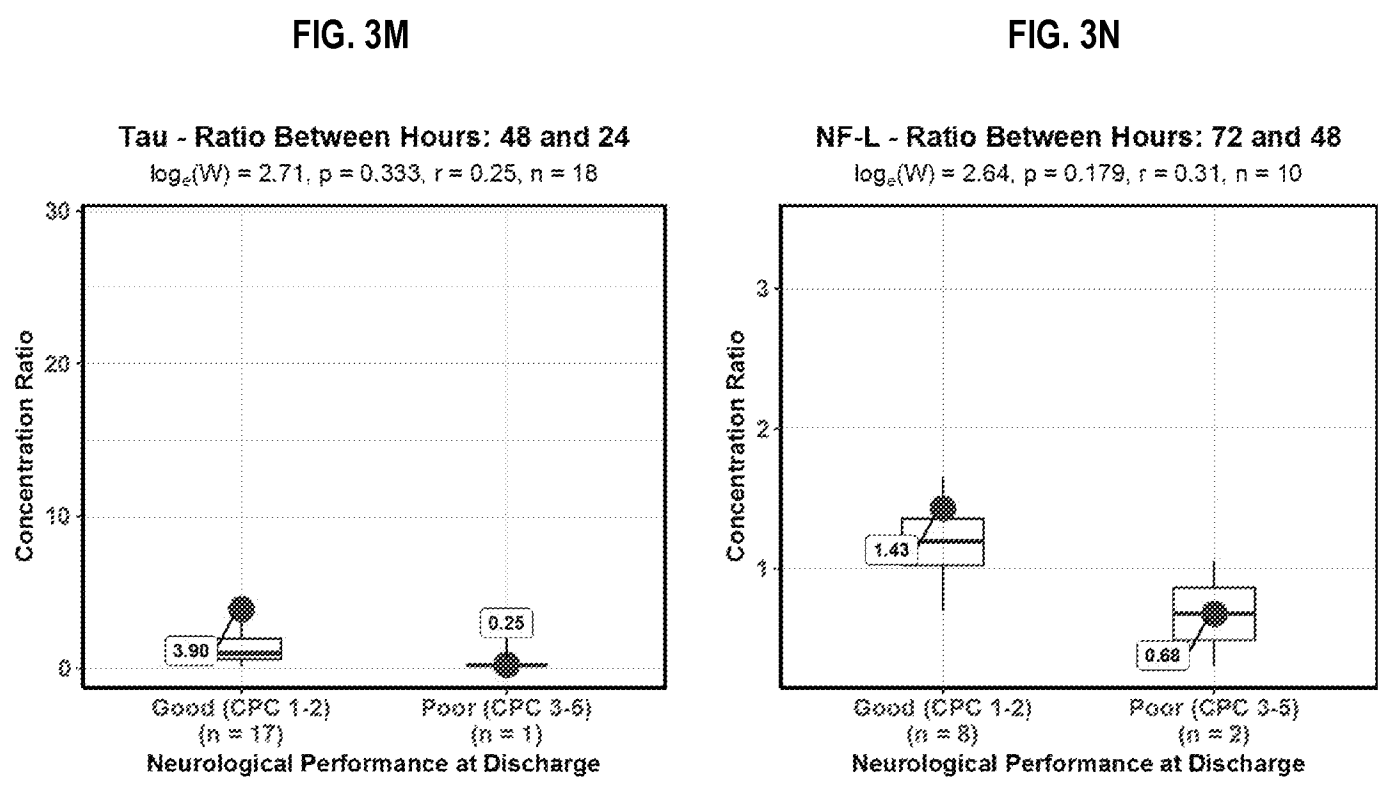

Outcomes were recorded, including cerebral performance category (CPC), mortality at discharge and mortality at 6 months. Associations between sepsis patients with and without AMS and outcomes were tested by Fisher's exact test and Mann-Whitney U-test (see Table 1 and Table 2, below). Receiver operator characteristics curves were created to evaluate the utility of biomarker concentrations or relative concentration changes from baseline in the identification of sepsis associated encephalopathy (cohort assignment), neurological functioning at discharge (CPC score), and six-month survival. Estimates of the areas under the curves (AUC) were obtained, where significant utility was defined as an AUC>0.5 at alpha=0.05. Measures demonstrating significant utility were further assessed for criterion measures (cutoffs) that maximizes sensitivity and specificity. Potential cutoff points were defined by the Youden's J statistic and classification performance was assessed by the sensitivity (Sens.), specificity (Spec.), positive predictive value (PPV), and negative predictive value (NPV). (See Table 3, Table 4 and Table 5). Boxplots corresponding to significant AUC measures were created and assessed using Mann-Whitney U test (see FIG. 2, FIG. 3, and FIG. 4). Repeated ROC analysis was performed using combinations of biomarkers to detect discriminatory utility in assessing outcomes (see Table 9). Generalized estimating equations, adjusted for within-subject correlation, were used to assess differences in biomarker kinetics and outcomes (see FIG. 5 and FIG. 6).

Of the 23 sepsis patients recruited, 11 (47.8%) presented with AMS and 12 (52.2%) presented without AMS. The mean age of the AMS cohort (cohort 1) was 70.3 years (95% CI 58-82), versus the non-AMS 51.7 years (95% CI 40-63) (p=0.023). There was no difference in sex, race, ethnicity, or APACHE II score at baseline observed. Subjects with AMS were less likely to have a favorable CPC score (1 or 2) at discharge compared to subjects without AMS (54.6% vs 100.0%, p=0.014). The 6-month mortality rate with and without AMS was 50% and 10% (p=0.140), respectively. The acute presentation of SAE is associated with compromised cognitive functioning at hospital discharge. See Table 2 and Table 3, below.

TABLE 1

Demographics of Study Population by Cohorts at Enrollment.

| | Total* (n = 26) | Cohort 1 (n = 11) | Cohort 2 (n = 12) | P value |
|---|---|---|---|---|
| Age (years) | 60.3 + 19.1 | 70.3 + 18.3 | 51.7 + 18.4 | 0.032 |
| Gender | | | | 0.999 |
| Male | 10 (38.5%) | 4 (36.4%) | 5 (41.7%) | |
| Female | 16 (61.5%) | 7 (63.6%) | 7 (58.3%) | |
| Racial Group | | | | 0.317 |
| African American | 6 (23.1%) | 1 (9.1%) | 4 (33.3%) | |
| White | 20 (76.9%) | 10 (90.9%) | 8 (66.7%) | |
| Body Mass Index (BMI) | 27.8 + 8.7 | 25.3 + 4.3 | 28.3 + 10.1 | 0.381 |
| APACHE II Score (Baseline) | 16.8 + 6.3 | 19.5 + 8.4 | 15.2 + 3.5 | 0.156 |

*Includes Cohort 3 Subjects

TABLE 2

Primary Outcomes by Cohort Assignment at Enrollment.

| | Total* (n = 26) | Cohort 1 (n = 11) | Cohort 2 (n = 12) | P value |
|---|---|---|---|---|
| CPC Score Discharge | | | | 0.008 |
| 1-2 (Good) | 18 (78.3%) | 6 (54.5%) | 12 (100%) | |
| 3-5 (Poor) | 5 (21.7%) | 45.5%) | 0 (0%) | |
| Survival to Discharge | | | | 0.217 |
| Yes | 24 (92.3%) | 9 (81.8%) | 12 (100%) | |
| No | 2 (7.7%) | 2 (18.2%) | 0 (0%) | |
| Survival to 6 Months | | | | 0.141 |
| Yes | 17 (73.9%) | 5 (50%) | 9 (90%) | |
| No | 6 (26.1%) | 5 (50%) | 1 (10%) | |

*Includes Cohort 3 Subjects

Of the biomarker measures analyzed 78 absolute and relative biomarker measures analyzed, 19, 17, and 16 demonstrated discriminatory utility, as defined by significant AUC, in the prediction of sepsis associated encephalopathy (cohort assignment), poor neurological performance at discharge (CPC score), and six-month mortality. Cutoffs and cutoff performance for concentration measures (for single-time point analysis) and ratios (for relative concentration change analysis) are displayed. See Tables 3-8, and the discussion below.

A. pNFH

Table 3: at the presentation of sepsis, a serum value greater than 168.9 pg/mL significantly aids in the diagnosis of a patient with sepsis associated encephalopathy (cohort 1).

Table 4: the ratio between the concentrations measured at approximately 24 hours or 72 hours after presentation and at baseline of less than 0.990 or 0.978, respectively, can significantly aid in the diagnosis of a patient with sepsis associated encephalopathy (cohort 1).

Table 5: at the presentation of sepsis, 48 hours or 72 hours levels over 212, 209, or 280 pg/ml respectively can significantly differentiate a neurologically intact patient who will be discharged from the hospital with a low CPC and more favorable neurologic outcome from those with a high CPC score of 3-5 defined as a severe cognitive deficit (3), coma (4), or death.

Table 6: the ratio between the concentrations at 6, 18, or 24 hours and baseline of less than of 0.979, 0.976, or 0.974 respectively, can significantly differentiate a neurologically intact patient who will be discharged from the hospital with a low CPC and more favorable neurologic outcome from those with a high CPC score of 3-5 defined as a severe cognitive deficit (3), coma (4), or death.

Table 7: at the presentation of sepsis, a serum value greater than>211.9 pg/mL can potentially aid in the prognosis of death within six months.

Table 8: the ratio between the concentration measured in time points 48 and 24 hours of greater than 1.013 can significantly prognosticate the outcome of death within six months.

S100B

Table 3: at approximately 72 hours following the presentation of sepsis, a level less than 32.2 pg/mL significantly aids in the diagnosis of a patient with sepsis associated encephalopathy (cohort 1).

Table 4: the ratio between the concentrations measured at approximately 72 hours after presentation and at baseline of less than 0.264 can significantly aid in the diagnosis of a patient with sepsis associated encephalopathy (cohort 1).

Table 6: the ratio between the concentrations at 72 hours and baseline of less than of 0.264 can significantly differentiate a neurologically intact patient who will be discharged from the hospital with a low CPC and more favorable neurologic outcome from those with a high CPC score of 3-5 defined as a severe cognitive deficit (3), coma (4), or death.

The ratio between the concentrations at 72 hours and 48 hours of less than of 0.201 can significantly differentiate a neurologically intact patient who will be discharged from the hospital with a low CPC and more favorable neurologic outcome from those with a high CPC score of 3-5 defined as a severe cognitive deficit (3), coma (4), or death. See Table 6.

Table 8: the ratio between the concentration measured in time points 48 and 24 hours, or 72 and 28 hours of less than 0.927 or 0.203 respectively, can significantly prognosticate the outcome of death within six months.

ratio between the concentrations at 72 hours and baseline of greater than of 0.264 can significantly prognosticate the outcome of death within six months. See Table 8.

UCHL-1

Table 3: at baseline, 6, 12, 18, 24, 48, or 72 hours following the presentation of sepsis, a level greater than 40.1, 40.5, 36.1, 37.1, 91.0, 30.8, or 32.4 pg/mL respectively, significantly aids in the diagnosis of a patient with sepsis associated encephalopathy (cohort 1).

Table 4: the ratio between the concentrations measured at approximately 24 hours and 18 hours after presentation of less than 0.775 can significantly aid in the diagnosis of a patient with sepsis associated encephalopathy (cohort 1).

Table 6: the ratio between the concentrations at 24 hours and 18 hours, or 48 hours and 24 hours, of less than of 0.765 or 0.657 respectively can significantly differentiate a neu-rologically intact patient who will be discharged from the hospital with a low CPC and more favorable neurologic outcome from those with a high CPC score of 3-5 defined as a severe cognitive deficit (3), coma (4), or death.

GFAP

Table 4: the ratio between the concentrations measured at approximately 18, 24, or 48 hours and at baseline of greater than 1.150, 1.025, or 0.780, respectively, can significantly aid in the diagnosis of a patient with sepsis associated encephalopathy (cohort 1)

Table 6: the ratio between the concentrations at 48 hours and 24 hours of less than of 0.676 can significantly differ-entiate a neurologically intact patient who will be discharged from the hospital with a low CPC and more favorable neurologic outcome from those with a high CPC score of 3-5 defined as a severe cognitive deficit (3), coma (4), or death.

Table 8: the ratio between the concentrations at 48 hours and baseline of greater than of 0.994 can significantly prognosticate the outcome of death within six months.

Tau

Table 5: at approximately 24 hours following the presen-tation, a level above 14.5 can differentiate a neurologically intact patient who will be discharged from the hospital with a low CPC and more favorable neurologic outcome from those with a high CPC score of 3-5 defined as a severe cognitive deficit (3), coma (4), or death.

Table 6: the ratio between the concentrations at 24 hours and 18 hours, or 48 hours and 24 hours, of greater than of 2.274 or less than 0.250 respectively can significantly dif-ferentiate a neurologically intact patient who will be dis-charged from the hospital with a low CPC and more favorable neurologic outcome from those with a high CPC score of 3-5 defined as a severe cognitive deficit (3), coma (4), or death.

Table 7: concentration at 24 hours greater than 1.64 or at 72 hours of greater than 0.63 can significantly prognosticate the outcome of death within six months.

Table 8: the ratio between the concentrations at 24 hours and 18 hours, or 48 and 24 hours, of greater than of 1.247 or less than 0.711 respectively, can significantly prognosti-cate the outcome of death within six months.

NF-L

Table 4: the ratio between the concentrations measured at approximately 12, 18, or 24 hours and at baseline of greater than 1.064, 1.132, or 1.122, respectively, can significantly aid in the diagnosis of a patient with sepsis associated encephalopathy (cohort 1).

Table 6: the ratio between the concentrations at 12 or 24 hours and baseline of greater than of 1.081 or 1.287 respec-tively, can significantly differentiate a neurologically intact patient who will be discharged from the hospital with a low CPC and more favorable neurologic outcome from those with a high CPC score of 3-5 defined as a severe cognitive deficit (3), coma (4), or death.

The ratio between the concentrations at 72 hours and 48 hours of less than of 1.053 can significantly differentiate a neurologically intact patient who will be discharged from the hospital with a low CPC and more favorable neurologic outcome from those with a high CPC score of 3-5 defined as a severe cognitive deficit (3), coma (4), or death. See Table 6.

Table 7: a serum value measured at 6 and 12 hours after presentation of greater than 95.4 and 54.3 pg/mL can poten-tially aid in the prognosis of death within six months.

Table 8: the ratio between the concentration measured in time points 72 and 48 hours of less than 1.053 can signifi-cantly prognosticate the outcome of death within six months. The ratio between the concentrations at 12 24, or 48 hours and baseline of greater than of 1.081, 1.287, or 1.103 respectively, can significantly prognosticate the outcome of death within six months.

TABLE 3

| Area under ROC Curve and Cutpoints Using Absolute Biomarker Concentrations for Diagnosis of Sepsis Associated Encephalopathy (Cohort 1 vs 2). | | | | | | | | |
|---|---|---|---|---|---|---|---|---|
| Biomarker (collection time)* | AUC (95CI) | P Value | Cutpoint (pg/mL) | Sens. (%) | Spec. (%) | PPV (%) | NPV (%) | Sample Size (n) |
| pNFH | | | | | | | | |
| (Baseline) | 0.73 (.55-.97) | 0.016 | >168.9 | 90.9 | 58.3 | 66.7 | 87.5 | 23 |
| S100B | | | | | | | | |
| (H72) | 0.87 (.64-.99) | 0.002 | <32.2 | 80.0 | 83.3 | 80.0 | 83.3 | 11 |
| UCHL-1 | | | | | | | | |
| (Baseline) | 0.87 (.73-.99) | <0.001 | >40.1 | 100.0 | 58.3 | 68.8 | 100.0 | 23 |
| (H06) | 0.80 (.60-.99) | 0.002 | >40.5 | 90.9 | 75.0 | 71.4 | 90.0 | 23 |
| (H12) | 0.84 (.67-.99) | <0.001 | >36.1 | 100.0 | 66.7 | 71.4 | 100.0 | 22 |
| (H18) | 0.84 (.66-.99) | <0.001 | >37.1 | 100.0 | 63.6 | 71.4 | 100.0 | 21 |
| (H24) | 0.86 (.67-.99) | <0.001 | >91.0 | 71.4 | 88.9 | 83.3 | 80.0 | 16 |
| (H48) | 0.88 (.69-.99) | <0.001 | >30.8 | 100.0 | 71.4 | 77.8 | 100.0 | 14 |
| (H72) | 0.80 (.50-.99) | 0.052 | >32.4 | 100.0 | 60.0 | 71.4 | 100.0 | 10 |

*Collection Time refers to the time in hours (H) at which the sample was obtained from the subject.

TABLE 4

Area under ROC Curve and Cutpoints Using Relative Change in Biomarker
Concentrations for Diagnosis of Sepsis Associated Encephalopathy (Cohort 1 vs 2).

| Biomarker (collection time)* | AUC (95CI) | P Value | Cutpoint (ratio) | Sens. (%) | Spec. (%) | PPV (%) | NPV (%) | Sample Size (n) |
|---|---|---|---|---|---|---|---|---|
| pNFH | | | | | | | | |
| (H24-Baseline) | 0.81 (.60-.99) | 0.004 | <0.990 | 87.5 | 72.7 | 70.0 | 88.9 | 19 |
| (H72-Baseline) | 0.89 (.66-.99) | <0.001 | <0.978 | 83.3 | 100.0 | 100.0 | 85.7 | 12 |
| S100B | | | | | | | | |
| (H72-Baseline) | 0.80 (.51-.99) | 0.048 | <0.264 | 60.0 | 100.0 | 100.0 | 75.0 | 11 |
| UCHL-1 | | | | | | | | |
| (H24-H18) | 0.78 (.53-.99) | 0.029 | <0.775 | 85.7 | 77.8 | 75.0 | 87.5 | 16 |
| GFAP | | | | | | | | |
| (H18-Baseline) | 0.77 (.52-.99) | 0.035 | >1.150 | 70.0 | 100.0 | 100.0 | 80.0 | 22 |
| (H24-Baseline) | 0.77 (.53-.99) | 0.028 | >1.025 | 75.0 | 81.8 | 75.0 | 81.8 | 19 |
| (H48-Baseline) | 0.80 (.59-.99) | 0.008 | >0.780 | 100.0 | 60.0 | 66.7 | 100.0 | 18 |
| NF-L | | | | | | | | |
| (H12-Baseline) | 0.84 (.67-.99) | <0.001 | >1.064 | 80.0 | 83.3 | 80.0 | 83.3 | 22 |
| (H18-Baseline) | 0.76 (.51-.99) | 0.039 | >1.132 | 80.0 | 81.8 | 80.0 | 81.8 | 21 |
| (H24-Baseline) | 0.77 (.54-.99) | 0.022 | >1.122 | 75.0 | 81.8 | 75.0 | 81.8 | 19 |

*Collection Time 2-Collection Time 1 in the first column] indicates that the change in biomarker concentration from collection time 1 to collection time 2, expressed as a ratio (T2/T1), was used for the analysis.

TABLE 5

Area under ROC Curve and Cutpoints Using Absolute Biomarker Concentrations for Prognosticating
Poor Neurological Performance (CPC 3-5) vs Good Neurological Performance (CPC 1-2) at Discharge.

| Biomarker (collection time)* | AUC (95CI) | P Value | Cutpoint (pg/mL) | Sens. (%) | Spec. (%) | PPV (%) | NPV (%) | Sample Size (n) |
|---|---|---|---|---|---|---|---|---|
| pNFH | | | | | | | | |
| (Baseline) | 0.77 (.55-.99) | 0.018 | >211.9 | 80.0 | 71.4 | 40.0 | 93.8 | 26 |
| (H48) | 0.87 (.58-.99) | 0.012 | >209.1 | 100.0 | 73.3 | 33.3 | 100.0 | 17 |
| (H72) | 0.91 (.71-.99) | <0.001 | >280.0 | 100.0 | 72.7 | 40.0 | 100.0 | 13 |
| Tau | | | | | | | | |
| (H24) | 0.89 (.67-.99) | <0.001 | >14.5 | 50.0 | 100.0 | 100.0 | 95.0 | 21 |

*Collection Time refers to the time in hours (H) at which the sample was obtained from the subject.

TABLE 6

Area under ROC Curve and Cutpoints Using Relative Change in Biomarker
Concentrations for Prognosticating Poor Neurological Performance (CPC 3-5) vs Good
Neurological Performance (CPC Score 1-2) at Discharge.

| Biomarker (collection time)* | AUC (95CI) | P Value | Cutpoint (ratio) | Sens. (%) | Spec. (%) | PPV (%) | NPV (%) | Sample Size (n) |
|---|---|---|---|---|---|---|---|---|
| pNFH | | | | | | | | |
| (H06-Baseline) | 0.83 (.67-.98) | <0.001 | <0.979 | 100.0 | 76.2 | 50.3 | 100.0 | 26 |
| (H18-Baseline) | 0.77 (.57-.97) | 0.007 | <0.976 | 100.0 | 61.9 | 33.2 | 100.0 | 25 |
| (H24-Baseline) | 0.87 (.68-.99) | <0.001 | <0.974 | 100.0 | 72.2 | 37.5 | 100.0 | 21 |
| S100B | | | | | | | | |
| (H72-Baseline) | 0.91 (.69-.99) | <0.001 | <0.264 | 100.0 | 81.8 | 50.0 | 100.0 | 13 |
| (H72-H48) | 0.99 (.99-.99) | <0.001 | <0.201 | 100.0 | 100.0 | 100.0 | 100.0 | 13 |
| UCHL-1 | | | | | | | | |
| (H48-H24) | 0.83 (.61-.99) | 0.003 | <0.657 | 100.0 | 83.3 | 33.3 | 100.0 | 13 |
| (H24-H12) | 0.72 (.49-.95) | 0.059 | <0.765 | 100.0 | 68.8 | 28.6 | 100.0 | 18 |

TABLE 6-continued

Area under ROC Curve and Cutpoints Using Relative Change in Biomarker
Concentrations for Prognosticating Poor Neurological Performance (CPC 3-5) vs Good
Neurological Performance (CPC Score 1-2) at Discharge.

| Biomarker (collection time)* | AUC (95CI) | P Value | Cutpoint (ratio) | Sens. (%) | Spec. (%) | PPV (%) | NPV (%) | Sample Size (n) |
|---|---|---|---|---|---|---|---|---|
| GFAP | | | | | | | | |
| (H48-H24) | 0.88 (.72-.99) | <0.001 | <0.676 | 100.0 | 88.2 | 33.3 | 100.0 | 18 |
| Tau | | | | | | | | |
| (H24-H18) | 0.92 (.80-.99) | <0.001 | >2.274 | 100.0 | 89.5 | 50.0 | 100.0 | 21 |
| (H48-H24) | 0.88 (.72-.99) | <0.001 | <0.250 | 100.0 | 88.2 | 33.3 | 100.0 | 18 |
| NF-L | | | | | | | | |
| (H72-H48) | 0.88 (.58-.99) | 0.012 | <1.053 | 100.0 | 75.0 | 50.0 | 100.0 | 10 |
| (H12-Baseline) | 0.81 (.63-.99) | <0.001 | >1.081 | 100.0 | 66.7 | 36.4 | 100.0 | 25 |
| (H24-Baseline) | 0.84 (.60-.99) | 0.006 | >1.287 | 100.0 | 73.7 | 28.6 | 100.0 | 21 |

*Collection Time 2-Collection Time 1 in the first column] indicates that the change in biomarker concentration from collection time 1 to collection time 2, expressed as a ratio (T2/T1), was used for the analysis.

TABLE 7

Area under ROC Curve and Cutpoints Using Absolute Biomarker Concentrations for
Prognosticating Six-Month Mortality.

| Biomarker (collection time)* | AUC (95CI) | P Value | Cutpoint (pg/mL) | Sens. (%) | Spec. (%) | PPV (%) | NPV (%) | Sample Size (n) |
|---|---|---|---|---|---|---|---|---|
| pNFH | | | | | | | | |
| (Baseline) | 0.75 (.50-.99) | 0.052 | >211.9 | 66.7 | 76.5 | 50.0 | 86.7 | 23 |
| Tau | | | | | | | | |
| (H24) | 0.80 (.53-.99) | 0.027 | >1.64 | 100.0 | 60.0 | 33.3 | 100.0 | 18 |
| (H72) | 0.83 (.56-.99) | 0.019 | >0.63 | 100.0 | 62.5 | 50.0 | 100.0 | 11 |
| NF-L | | | | | | | | |
| (H06) | 0.73 (.48-.97) | 0.068 | >95.4 | 66.7 | 87.5 | 66.7 | 87.5 | 22 |
| (H12) | 0.75 (.50-.99) | 0.048 | >54.3 | 80.0 | 70.6 | 44.4 | 92.3 | 22 |

*Collection Time refers to the time in hours (H) at which the sample was obtained from the subject.

TABLE 8

Area under ROC Curve and Cutpoints Using Relative Changes in Biomarker
Concentrations for Prognosticatinl Six-Month Mortality.

| Biomarker (collection time)* | AUC (95CI) | P Value | Cutpoint (ratio) | Sens. (%) | Spec. (%) | PPV (%) | NPV (%) | Sample Size (n) |
|---|---|---|---|---|---|---|---|---|
| pNFH | | | | | | | | |
| (H48-H24) | 0.83 (.59-.99) | 0.008 | >1.013 | 100.0 | 70.0 | 50.0 | 100.0 | 13 |
| S100B | | | | | | | | |
| (H48-H24) | 0.85 (.63-.99) | 0.002 | <0.927 | 100.0 | 76.9 | 50.0 | 100.0 | 16 |
| (H72-H48) | 0.99 (.99-.99) | <0.001 | <0.203 | 100.0 | 100.0 | 100.0 | 100.0 | 9 |
| (H72-Baseline) | 0.94 (.79-.99) | <0.001 | <0.264 | 100.0 | 88.9 | 66.7 | 100.0 | 11 |
| GFAP | | | | | | | | |
| (H48-Baseline) | 0.82 (.56-.99) | 0.014 | >0.994 | 100.0 | 61.5 | 37.5 | 100.0 | 16 |
| Tau | | | | | | | | |
| (H24-H18) | 0.89 (.70-.99) | <0.001 | >1.247 | 100.0 | 73.3 | 42.9 | 100.0 | 18 |
| (H48-H24) | 0.81 (.52-.99) | 0.036 | <0.711 | 100.0 | 69.2 | 33.3 | 100.0 | 15 |
| NF-L | | | | | | | | |
| (H72-H48) | 0.86 (.52-.99) | 0.034 | <1.053 | 100.0 | 71.4 | 50.0 | 100.0 | 9 |
| (H12-Baseline) | 0.84 (.66-.99) | <0.001 | >1.081 | 100.0 | 64.7 | 45.5 | 100.0 | 22 |

TABLE 8-continued

Area under ROC Curve and Cutpoints Using Relative Changes in Biomarker
Concentrations for Prognosticatinl Six-Month Mortality.

| Biomarker (collection time)* | AUC (95CI) | P Value | Cutpoint (ratio) | Sens. (%) | Spec. (%) | PPV (%) | NPV (%) | Sample Size (n) |
|---|---|---|---|---|---|---|---|---|
| (H24-Baseline) | 0.87 (.68-.99) | <0.001 | >1.287 | 100.0 | 73.3 | 42.9 | 100.0 | 18 |
| (H48-Baseline) | 0.79 (.55-.99) | 0.017 | >1.103 | 100.0 | 64.3 | 37.5 | 100.0 | 17 |

*Collection Time 2-Collection Time 1 in the first column] indicates that the change in biomarker concentration from collection time 1 to collection time 2, expressed as a ratio (T2/T1), was used for the analysis.

Example 2. Methods of Use

Since GFAP, UCHL-1, S100B, pNFH, NF-L, and Tau demonstrate unique kinetic biomarker profiles, combining the concentration of two biomarkers should result at baseline (6 hours from ED arrival) and the sample collected at 72 hours will yield improved diagnostic and/or prognostic utility as demonstrated by the Area Under the ROC Curve (AUC) data. Comparisons between the combination AUC and both biomarkers alone was performed using a chi-square distribution test, $\chi^2=(AUC_{combined}-AUC_{alone})^2/(s_{combined}^2+s_{alone}^2)$, where $AUC_{combined}$ is the area under the curve for the combined biomarker measurement, $AUC_{alone}$ is the single biomarker measurement, and $s_{combined}^2$ and $s_{alone}^2$ are the respective standard errors. The P-value then was obtained using the calculated $\chi2$ statistic with one degree freedom. See Tables 9 and 10.

Combining the concentrations obtained from GFAP and UCHL-1 simultaneously at baseline (6 hours from ED arrival) demonstrates the best utility in diagnosing SAE (AUC=0.93). See Table 9, which is significantly better each AUC for each marker alone (0.61 for GFAP; 0.87 for UCH-L1). Similarly, for prognosticating poor neurological Performance (CPC 3-5) vs good neurological performance (CPC Score 1-2) at discharge, combining the concentrations obtained from GFAP and Tau simultaneously at baseline (6 hours from ED arrival) yields a AUC=0.85, which is better than AUC for GFAP alone 0.61 and AUC for Tau alone 0.59 (see Table 9). For 72 hour biomarker levels, combination of NF-L and pNFH yielded an AUC of 0.99 to diagnosing SAE, which is superior to NF-L (AUC=0.71) and pNFH (AUC=0.61) alone (see Table 10). Lastly, for prognosticating patient mortality at 6 months, combination of 72 hour post-sepsis levels of GFAP+S100B has the highest AUC (AUC 0.99), when compared to GFAP alone (AUC=0.67) and S100B (AUC=0.67) alone (see Table 10).

TABLE 9

Area under ROC Curve Using Combined Biomarker Concentrations for
Diagnosing and Prognosticating Outcomes at Baseline.

| Biomarker 1 + Biomarker 2 | Biomarker 1 Alone | | Biomarker 2 Alone | | Combination | | Combination vs. biomarker 1 | Combination vs. biomarker 2 |
|---|---|---|---|---|---|---|---|---|
| | AUC (95CI) | P Value | AUC (95CI) | P Value | AUC (95CI) | P Value | P Value | P Value |
| SAE Diagnosis | | | | | | | | |
| GFAP + NF-L | 0.61 (.38-.85) | 0.356 | 0.67 (.45-.90) | 0.157 | 0.80 (.61-.98) | 0.002 | 0.246 | 0.423 |
| GFAP + UCHL-1 | 0.61 (.38-.85) | 0.356 | 0.87 (.73-.99) | <0.001 | 0.93 (.83-.99) | <0.001 | 0.018 | 0.498 |
| GFAP + S100B | 0.61 (.38-.85) | 0.356 | 0.67 (.43-.72) | 0.157 | 0.76 (.56-.96) | 0.013 | 0.371 | 0.614 |
| GFAP + pNFH | 0.61 (.38-.85) | 0.356 | 0.76 (.55-.97) | 0.016 | 0.78 (.56-.98) | 0.006 | 0.299 | 0.878 |
| NF-L + UCHL-1 | 0.67 (.45-.90) | 0.157 | 0.87 (.73-.99) | <0.001 | 0.88 (.73-.99) | <0.001 | 0.144 | 0.943 |
| NF-L + Tau | 0.67 (.45-.90) | 0.157 | 0.56 (.31-.81) | 0.622 | 0.72 (.50-.94) | 0.051 | 0.918 | 0.366 |
| NF-L + pNFH | 0.67 (.45-.90) | 0.157 | 0.76 (.55-.97) | 0.016 | 0.71 (.49-.93) | 0.065 | 0.817 | 0.772 |
| UCHL-1 + Tau | 0.87 (.73-.99) | <0.001 | 0.56 (.31-.81) | 0.622 | 0.89 (.76-.99) | <0.001 | 0.749 | 0.026 |
| UCHL-1 + S100B | 0.87 (.73-.99) | <0.001 | 0.67 (.43-.72) | 0.157 | 0.87 (.73-.99) | <0.001 | 1.000 | 0.186 |
| UCHL-1 + pNFH | 0.87 (.73-.99) | <0.001 | 0.76 (.55-.97) | 0.016 | 0.89 (.75-.99) | <0.001 | 0.880 | 0.312 |
| Tau + pNFH | 0.56 (.31-.81) | 0.622 | 0.76 (.55-.97) | 0.016 | 0.74 (.53-.96) | 0.015 | 0.244 | 0.869 |
| Neurological Performance at Discharge | | | | | | | | |
| GFAP + Tau | 0.61 (.38-.85) | 0.454 | 0.59 (.29-.90) | 0.541 | 0.85 (.70-.99) | <0.001 | 0.130 | 0.173 |
| Six-Month Mortality | | | | | | | | |
| GFAP + pNFH | 0.49 (.38-.85) | 0.944 | 0.75 (.50-.99) | 0.052 | 0.75 (.49-.99) | 0.074 | 0.201 | 1.000 |
| UCHL-1 + pNFH | 0.38 (.14-.63) | 0.358 | 0.75 (.50-.99) | 0.052 | 0.74 (.48-.99) | 0.069 | 0.051 | 0.954 |
| Tau + pNFH | 0.50 (.19-.81) | 1.000 | 0.75 (.50-.99) | 0.052 | 0.77 (.56-.98) | 0.017 | 0.181 | 0.950 |

"Biomarker 1" = First biomarker listed,
"Biomarker 2" = Second biomarker listed.

TABLE 10

Area under ROC Curve Using Combined Biomarker Concentrations for
Diagnosing and Prognosticating Outcomes at 72 Hours

| Biomarker 1 + Biomarker 2 | Biomarker 1 Alone | | Biomarker 2 Alone | | Combination | | Combination vs. biomarker 1 | Combination vs. biomarker 2 |
|---|---|---|---|---|---|---|---|---|
| | AUC (95CI) | P Value | AUC (95CI) | P Value | AUC (95CI) | P Value | P Value | P Value |
| SAE Diagnosis | | | | | | | | |
| NF-L + UCHL-1 | 0.71 (.37-.99) | 0.273 | 0.80 (.50-.99) | 0.052 | 0.85 (.59-.99) | 0.011 | 0.665 | 1.000 |
| NF-L + S100B | 0.71 (.37-.99) | 0.273 | 0.87 (.64-.99) | 0.002 | 0.83 (.54-.99) | 0.025 | 0.815 | 0.815 |
| NF-L + pNFH | 0.71 (.37-.99) | 0.273 | 0.61 (.27-.95) | 0.522 | 0.99 (.99-.99) | <0.001 | 0.480 | 0.371 |
| UCHL-1 + Tau | 0.80 (.50-.99) | 0.052 | 0.70 (.37-.99) | 0.273 | 0.80 (.51-.99) | 0.0528 | 1.000 | 1.000 |
| UCHL-1 + S100B | 0.80 (.50-.99) | 0.052 | 0.87 (.64-.99) | 0.002 | 0.99 (.99-.99) | <0.001 | 0.278 | 0.394 |
| UCHL-1 + pNFH | 0.80 (.50-.99) | 0.052 | 0.61 (.27-.95) | 0.522 | 0.81 (.48-.99) | 0.065 | 0.814 | 0.814 |
| Tau + S100B | 0.70 (.37-.99) | 0.273 | 0.87 (.64-.99) | 0.002 | 0.88 (.63-.99) | 0.004 | 0.573 | 0.831 |
| S100B + pNFH | 0.87 (.64-.99) | 0.002 | 0.61 (.27-.95) | 0.522 | 0.99 (.99-.99) | <0.001 | 0.480 | 0.074 |
| Neurological Performance at Discharge | | | | | | | | |
| GFAP + NF-L | 0.73 (.46-.99) | 0.237 | 0.63 (.32-.94) | 0.518 | 0.89 (.70-.99) | <0.001 | 0.387 | 0.188 |
| GFAP + Tau | 0.73 (.46-.99) | 0.237 | 0.77 (.47-.99) | 0.176 | 0.83 (.49-.99) | 0.058 | 0.664 | 0.785 |
| GFAP + S100B | 0.73 (.46-.99) | 0.237 | 0.64 (.20-.99) | 0.554 | 0.99 (.99-.99) | <0.001 | 0.073 | 0.209 |
| GFAP + pNFH | 0.73 (.46-.99) | 0.237 | 0.91 (.71-.99) | <0.001 | 0.93 (.73-.99) | <0.001 | 0.277 | 0.893 |
| NF-L + UCHL-1 | 0.63 (.32-.94) | 0.518 | 0.74 (.45-.99) | 0.229 | 0.79 (.50-.99) | 0.052 | 0.473 | 0.814 |
| NF-L + pNFH | 0.63 (.32-.94) | 0.518 | 0.91 (.71-.99) | <0.001 | 0.92 (.70-.99) | <0.001 | 0.163 | 0.961 |
| UCHL-1 + pNFH | 0.74 (.45-.99) | 0.229 | 0.91 (.71-.99) | <0.001 | 0.99 (.99-.99) | <0.001 | 0.096 | 0.383 |
| Tau + S100B | 0.77 (.47-.99) | 0.176 | 0.64 (.20-.99) | 0.554 | 0.99 (.99-.99) | <0.001 | 0.168 | 0.209 |
| Tau + pNFH | 0.77 (.47-.99) | 0.176 | 0.91 (.71-.99) | <0.001 | 0.93 (.74-.99) | <0.001 | 0.411 | 0.893 |
| S100B + pNFH | 0.64 (.20-.99) | 0.554 | 0.91 (.71-.99) | <0.001 | 0.99 (.99-.99) | <0.001 | 0.209 | 0.383 |
| Six-Month Mortality | | | | | | | | |
| GFAP + NF-L | 0.67 (.34-.99) | 0.414 | 0.67 (.35-.99) | 0.414 | 0.88 (.66-.99) | 0.001 | 0.326 | 0.312 |
| GFAP + Tau | 0.67 (.34-.99) | 0.414 | 0.83 (.56-.99) | 0.019 | 0.83 (.53-.99) | 0.061 | 0.509 | 1.000 |
| GFAP + S100B | 0.67 (.34-.99) | 0.414 | 0.67 (.27-.99) | 0.480 | 0.99 (.99-.99) | <0.001 | 0.062 | 0.185 |
| GFAP + pNFH | 0.67 (.34-.99) | 0.414 | 0.73 (.37-.99) | 0.262 | 0.92 (.70-.99) | <0.001 | 0.243 | 0.428 |
| NF-L + pNFH | 0.67 (.35-.99) | 0.414 | 0.73 (.37-.99) | 0.262 | 0.92 (.70-.99) | <0.001 | 0.230 | 0.428 |
| UCHL-1 + pNFH | 0.25 (.00-.55) | 0.221 | 0.73 (.37-.99) | 0.262 | 0.99 (.99-.99) | <0.001 | <0.001 | 0.187 |
| Tau + S100B | 0.83 (.56-.99 | 0.019 | 0.67 (.27-.99) | 0.480 | 0.99 (.99-.99) | <0.001 | 0.239 | 0.185 |
| Tau + pNFH | 0.83 (.56-.99) | 0.019 | 0.73 (.37-.99) | 0.262 | 0.92 (.70-.99) | <0.001 | 0.651 | 0.428 |
| S100B + pNFH | 0.67 (.27-.99) | 0.480 | 0.73 (.37-.99) | 0.262 | 0.99 (.99-.99) | <0.001 | 0.034 | 0.187 |

"Biomarker 1" = First biomarker listed,
"Biomarker 2" = Second biomarker listed.

After controlling for within-subject variation, a relative change in serum S100B concentration from baseline to 72 hours can significantly differentiate patients who will survive 6 months with a rise in concentration over time compared to those who will experience death with a relative decline in concentration over time. See FIG. 5.

After controlling for within-subject variation, pNFH serum concentrations are significantly lower among sepsis patients who will be discharged from the hospital with a low CPC and more favorable neurologic outcome compared with those with a high CPC score of 3-5 defined as a severe cognitive deficit (3), coma (4), or death. See FIG. 6.

FIG. 8 also shows higher levels if brain biomarker proteins over 0 h to 72 h in those Sepsis patients who have shown alerted mental status AMS (AMS) than those withoh: FIG. 8 shows that the mean and standard deviation of 6 brain biomarkers at different time points for sepsis patients with alerted mental status AMS (AMS), those without AMS and ncontrol subjects with no systemic inflammation. The subjects are categorized into three groups: (1) no systemic inflammation (control group), (2) sepsis without altered mental status (sepsis without AMS); and (3) sepsis with altered mental status (sepsis with AMS group). The levels of several biomarkers (most notably NF-L, UCH-L1, Tau, S100B) are higher at many time points in the sepsis with AMS group. Some of these have also achieve statistically significant differences between Group (3) and Group (2) also (* p<0.05). This example shows the unobvious utility of using single or combination of these brain biomarker proteins as blood tests at one or more than one time points to diagnose those sepsis patients who likely will develop altered mental status and thus likely suffer from sepsis associated encephalopathy and might require additional patient care or intervention.

Example 3. Patient Testing

Scenario 1.

A 50 year old otherwise healthy woman with a history of hypertension arrives with altered mentation. Her physical exam is remarkable for elevated heart rate (tachycardia) only and confusion. The physician proceeds to order a brain computed tomography scan, electrocardiogram, laboratory assays, and consults neurology with a working diagnosis of stroke, acute coronary syndrome, metabolic disturbance, and drug or illicit substance use. Four hours later, all studies are negative, and the patient remains altered.

The ED physician orders a panel of encephalopathy markers are sent demonstrating pNFH 202 pg/mL and UCHL-1 of 55 pg/mL suggesting encephalopathy from an acute illness such as sepsis or critical illness. The physician suspects occult sepsis. Blood and urine cultures are obtained, empiric intravenous antibiotics are initiated and the patient is admitted to the hospital. The following day, the patient's tachycardia has resolved and her behavior has returned to her baseline. 24 hours later the patient's blood cultures grow out *Escherichia coli* and her white blood cell count rises by 3 points.

Scenario 2.

An 85 year old man with a medical history of peripheral vascular disease, chronic obstructive pulmonary disease, and diabetes presents to the emergency department with slurred speech. This is alarming to his family who had just returned from vacation with him. He lives in an assisted living facility but has been fairly independent, values his autonomy, and plays golf regularly. In the emergency room, he quickly decompensates and the decision is made to intubate and place on a mechanical ventilator to help his breathing. The nurse informs the physician that the patient has a fever of 102.8, a chest X-ray demonstrates a pneumonia and initial laboratory tests are diagnostic of a sepsis diagnosis. Given his diagnosis of sepsis, the physicians order a panel of encephalopathy markers that are set to be trended every 12 hours for a total of 4 assays. His initial biomarkers results are pNFH 210 pg/mL UCHL-1 300 pg/mL suggesting acute critical illness encephalopathy. The following 2 days the patient remains on the ventilator and develops acute respiratory distress syndrome. The family grows increasingly anxious that he has not improved. The intensivist collects additional biomarkers to trend. On the $3^{rd}$ day of admission there is a 90% reduction in the S100B, a 43% reduction in GFAP since admission and a serum Tau concentration of 3.5 pg/mL. The intensivist shares the concerning news about the patient's condition. They recommend that 2 surgeries including a feeding tube and a tracheal tube placement be performed. The intensivist team also shares that the pattern of biomarkers not only suggests a devastating neurologic event as a result of the sepsis, but that he may not be capable of returning back to playing golf upon admission, and will likely need to be admitted to a nursing home. The family asks "Is he dying?" "How much time does he have?" The intensivist shares that even if he recovers from the sepsis well enough to be discharged, he will likely not survive beyond 6 months. The family declines the surgeries and convenes a family meeting to decide on withdrawal of care.

Scenario 3.

A 75 year old woman arrived to the emergency department and a sepsis alert is issued, alerting the department of the patient's arrival. The patient is unconscious and physicians are unaware of her mental status prior to arriving to the hospital. There are no family members available to provide information concerning whether the patient normally has dementia. Laboratory tests, a brain cat scan and a neurology consult is obtained. Results indicate an infection in present in her urine without any indication of a stroke or intracerebral hemorrhage. A UCHL-1 measurement is performed and the result is <40 pg/mL suggesting that she does not have sepsis associated encephalopathy. Providers return to the patient and perform a thorough exam and find 2 fentanyl patches on the patients left thigh. These patches are removed with improvement in the patient's mentation within hours.

REFERENCES

All references listed below and throughout the specification are hereby incorporated by reference in their entirety.

1. Korley et al., Performance evaluation of a multiplex assay for simultaneous detection of four clinically relevant traumatic brain injury biomarkers. Journal of Neurotrauma 2018; 36(1), 182-187.
2. Mondello S et al., Blood-based protein biomarkers for the management of traumatic brain injuries in adults presenting to emergency departments with mild brain injury: a living systematic review and meta-analysis. Journal of Neurotrauma 2018.
3. Wang K K, Yang Z, Zhu T, Shi Y, Rubenstein R, Tyndall J A, and Manley G T. An update on diagnostic and prognostic biomarkers for traumatic brain injury. Expert review of molecular diagnostics 2018; 18(2), 165-180.
4. Yao B, Zhang L N, and Ai Y H. Serum S1000 is a better biomarker than neuron-specific enolase for sepsis-associated encephalopathy and determining its prognosis: a prospective and observational study. Neurochemical research 2014; 39(7), 1263-1269.
5. Ehler J et al., The prognostic value of neurofilament levels in patients with sepsis-associated encephalopathy—A prospective, pilot observational study. PloS one 2019; 14(1), e0211184.
6. Ehler J et al., Translational evidence for two distinct patterns of neuroaxonal injury in sepsis: a longitudinal, prospective translational study. Critical Care 2017; 21(1), 262.
7. Martin G S, Mannino D M, Eaton S, Moss M. The epidemiology of sepsis in the United States from 1979 through 2000. N Engl J Med 2003; 348:1546-54.
8. Lagu T, Rothberg M B, Shieh M S, Pekow P S, Steingrub J S, Lindenauer P K. Hospitalizations, costs, and outcomes of severe sepsis in the United States 2003 to 2007. Crit Care Med 2012; 40:754-61.
9. Gofton T E, Young G B. Sepsis-associated encephalopathy. Nat Rev Neurol 2012; 8:557-66.
10. Eidelman L A, Putterman D, Putterman C, Sprung C L. The spectrum of septic encephalopathy. Definitions, etiologies, and mortalities. JAMA 1996; 275:470-3.
11. Annane D, Sharshar T. Cognitive decline after sepsis. Lancet Respir Med 2015; 3:61-9.
12. Iwashyna T J, Ely E W, Smith D M, Langa K M. Long-term cognitive impairment and functional disability among survivors of severe sepsis. JAMA 2010; 304:1787-94.
13. Widmann C N, Heneka M T. Long-term cerebral consequences of sepsis. Lancet Neurol 2014; 13:630-6.
14. Pratt A K, Chang J J, Sederstrom N O. A Fate Worse Than Death: Prognostication of Devastating Brain Injury. Crit Care Med 2019; 47:591-8.
15. Evans L R, Boyd E A, Malvar G, et al. Surrogate decision-makers' perspectives on discussing prognosis in the face of uncertainty. Am J Respir Crit Care Med 2009; 179:48-53.

The invention claimed is:

1. A method of improving diagnosis of sepsis-associated encephalopathy (SAE) in a subject diagnosed with or suspected of having sepsis, comprising:

(a) collecting a biological sample from the subject within about 6 hours from arrival at a treatment facility, within about 72 hours from arrival at a treatment facility, or both; and (b) testing the sample or samples for the presence or amount of a first biomarker and a second biomarker, wherein the first biomarker is selected from the group consisting of GFAP, UCH-L1, NF-L, and pNF-H; and the second biomarker is selected from the group consisting of GFAP, NF-L, pNF-H, UCH-L1, Tau, secretogranin, MBP, αII-spectrin, SBDP, NSE, BDNF, and Pro-BDNF; and (c) determining whether the subject has SAE or an increased likelihood thereof based on at least in part of the presence or amount of the first and second biomarkers measured in (b).

2. The method of claim 1, wherein the first biomarker is GFAP and the second biomarker is UCH-L1.

3. The method of claim 1, wherein the first biomarker is NF-L and the second biomarker is pNF-H.

\* \* \* \* \*